(12) United States Patent
Levinson et al.

(10) Patent No.: US 10,251,792 B2
(45) Date of Patent: Apr. 9, 2019

(54) METHODS AND DEVICES FOR SKIN TIGHTENING

(71) Applicant: Cytrellis Biosystems, Inc., Woburn, MA (US)

(72) Inventors: Douglas Levinson, Sherborn, MA (US); David Sean Stone, Acton, MA (US); Alec Ginggen, Medford, MA (US)

(73) Assignee: Cytrellis Biosystems, Inc., Woburn, MA (US)

( * ) Notice: Subject to any disclaimer, the term of this patent is extended or adjusted under 35 U.S.C. 154(b) by 0 days.

(21) Appl. No.: 15/905,421

(22) Filed: Feb. 26, 2018

(65) Prior Publication Data

US 2018/0185196 A1 Jul. 5, 2018

Related U.S. Application Data

(63) Continuation of application No. 14/764,866, filed as application No. PCT/US2014/016483 on Feb. 14, 2014.

(60) Provisional application No. 61/766,937, filed on Feb. 20, 2013.

(51) Int. Cl.
| | | |
|---|---|---|
| *A61F 13/00* | (2006.01) | |
| *A61F 13/02* | (2006.01) | |
| *A61B 17/3205* | (2006.01) | |
| *A61B 17/3209* | (2006.01) | |
| *A61M 35/00* | (2006.01) | |

(52) U.S. Cl.
CPC ...... *A61F 13/0246* (2013.01); *A61B 17/3205* (2013.01); *A61B 17/32093* (2013.01); *A61F 13/0233* (2013.01); *A61M 35/00* (2013.01); *A61F 2013/0028* (2013.01)

(58) Field of Classification Search
CPC .............. A61F 13/0246; A61F 13/0233; A61F 2013/0028; A61F 13/00; A61B 17/3205; A61B 17/32093; A61B 17/08; A61M 35/00
See application file for complete search history.

(56) References Cited

U.S. PATENT DOCUMENTS

| | | |
|---|---|---|
| 2,426,535 A | 8/1947 | Turkel |
| 3,001,522 A | 9/1961 | Silverman |
| 3,214,869 A | 11/1965 | Stryker |
| (Continued) | | |

FOREIGN PATENT DOCUMENTS

| | | |
|---|---|---|
| CA | 1275215 C | 10/1990 |
| CA | 2361777 A1 | 5/2002 |
| (Continued) | | |

OTHER PUBLICATIONS

Alsberg, E. et al., Engineering growing tissues, PNAS, 99(19):12025-12030 (2002).

(Continued)

*Primary Examiner* — Ophelia A Hawthorne
(74) *Attorney, Agent, or Firm* — Choate, Hall & Stewart LLP; Brenda Herschbach Jarrell; Alexander D. Augst

(57) ABSTRACT

The present invention relates to methods and devices for skin tightening after incising or excising tissue portions from a subject. Exemplary methods and devices include tunable dressings having an adhesive layer and a regulatable layer or an un-stretched layer that responds to one or more external stimuli to contract or expand the dressing, where the contraction or expansion can be uniform or non-uniform.

27 Claims, 4 Drawing Sheets

(56) References Cited

U.S. PATENT DOCUMENTS

| | | |
|---|---|---|
| 3,598,108 A | 8/1971 | Jamshidi et al. |
| 3,683,892 A | 8/1972 | Harris |
| 3,788,320 A | 1/1974 | Dye |
| 3,929,123 A | 12/1975 | Jamshidi |
| 4,108,096 A | 8/1978 | Ciecior |
| 4,159,659 A | 7/1979 | Nightingale |
| 4,403,617 A | 9/1983 | Tretinyak |
| 4,458,678 A | 7/1984 | Yannas et al. |
| 4,476,864 A | 10/1984 | Tezel |
| 4,604,346 A | 8/1986 | Bell et al. |
| 4,640,296 A | 2/1987 | Schnepp-Pesch et al. |
| 4,649,918 A | 3/1987 | Pegg et al. |
| D297,375 S | 8/1988 | Liu |
| 4,815,462 A | 3/1989 | Clark |
| 4,865,026 A | 9/1989 | Barrett |
| 4,903,709 A | 2/1990 | Skinner |
| D323,034 S | 1/1992 | Reinstein |
| 5,152,763 A | 10/1992 | Johnson |
| D338,070 S | 8/1993 | Lam |
| D342,138 S | 12/1993 | Wollman et al. |
| 5,269,316 A | 12/1993 | Spitalny |
| 5,306,490 A | 4/1994 | Barley, Jr. |
| 5,324,305 A | 6/1994 | Kanner |
| 5,331,972 A | 7/1994 | Wadhwani et al. |
| 5,415,182 A | 5/1995 | Chin et al. |
| 5,419,761 A | 5/1995 | Narayanan et al. |
| 5,439,475 A | 8/1995 | Bennett |
| 5,458,112 A | 10/1995 | Weaver |
| D377,404 S | 1/1997 | Izumi |
| 5,611,810 A | 3/1997 | Arnold et al. |
| 5,615,690 A | 4/1997 | Giurtino et al. |
| 5,639,654 A | 6/1997 | Bernard et al. |
| D388,543 S | 12/1997 | Eguchi et al. |
| 5,713,375 A | 2/1998 | McAllister |
| 5,749,895 A | 5/1998 | Sawyer et al. |
| 5,792,169 A | 8/1998 | Markman |
| 5,810,857 A | 9/1998 | Mackool |
| 5,827,297 A | 10/1998 | Boudjema |
| 5,868,744 A | 2/1999 | Willmen |
| 5,879,326 A | 3/1999 | Godshall et al. |
| 5,885,211 A | 3/1999 | Eppstein et al. |
| 5,885,226 A | 3/1999 | Rubinstein et al. |
| 5,902,319 A | 5/1999 | Daley |
| 5,922,000 A | 7/1999 | Chodorow |
| 5,925,002 A | 7/1999 | Wollman |
| 5,928,162 A | 7/1999 | Giurtino et al. |
| 5,931,855 A | 8/1999 | Buncke |
| 5,989,273 A | 11/1999 | Arnold |
| 6,022,324 A | 2/2000 | Skinner |
| D425,241 S | 5/2000 | Nishizawa et al. |
| 6,059,807 A | 5/2000 | Boudjema |
| 6,063,094 A | 5/2000 | Rosenberg |
| 6,178,346 B1 | 1/2001 | Amundson et al. |
| 6,197,039 B1 | 3/2001 | Ashraf |
| 6,211,598 B1 | 4/2001 | Dhuler et al. |
| 6,241,687 B1 | 6/2001 | Voegele et al. |
| 6,241,739 B1 | 6/2001 | Waldron |
| 6,251,097 B1 | 6/2001 | Kline et al. |
| 6,264,618 B1 | 7/2001 | Landi et al. |
| 6,342,213 B1 | 1/2002 | Barley et al. |
| D457,265 S | 5/2002 | Gebhard |
| D458,710 S | 6/2002 | Altamore et al. |
| 6,432,098 B1 | 8/2002 | Kline et al. |
| 6,440,086 B1 | 8/2002 | Hohenberg |
| 6,461,369 B1 | 10/2002 | Kim |
| 6,537,264 B1 | 3/2003 | Cormier et al. |
| 6,562,037 B2 | 5/2003 | Paton et al. |
| 6,669,618 B2 | 12/2003 | Reising et al. |
| 6,669,694 B2 | 12/2003 | Shadduck |
| 6,733,496 B2 | 5/2004 | Sharkey et al. |
| 6,733,498 B2 | 5/2004 | Paton et al. |
| D500,391 S | 12/2004 | Nielsen et al. |
| 6,881,203 B2 | 4/2005 | Delmore et al. |
| 6,887,250 B1 | 5/2005 | Dority et al. |
| 6,893,388 B2 | 5/2005 | Reising et al. |
| 6,936,039 B2 | 8/2005 | Kline et al. |
| D509,301 S | 9/2005 | Talbot et al. |
| 6,997,923 B2 | 2/2006 | Anderson et al. |
| 7,073,510 B2 | 7/2006 | Redmond et al. |
| 7,131,951 B2 | 11/2006 | Angel |
| D538,430 S | 3/2007 | Ohta |
| 7,651,507 B2 | 1/2010 | Mishra et al. |
| 7,658,728 B2 | 2/2010 | Yuzhakov |
| 7,926,401 B2 | 4/2011 | Mishra et al. |
| 8,128,639 B2 | 3/2012 | Tippett |
| 8,209,006 B2 | 6/2012 | Smith et al. |
| 8,226,664 B2 | 7/2012 | Drews et al. |
| 8,246,611 B2 | 8/2012 | Paithankar et al. |
| 8,435,791 B2 | 5/2013 | Galun et al. |
| 8,480,592 B2 | 7/2013 | Chudzik et al. |
| 8,696,686 B2 | 4/2014 | Drews et al. |
| 8,900,181 B2 | 12/2014 | Knowlton |
| 9,017,343 B2 | 4/2015 | Westerling, Jr. et al. |
| 9,060,803 B2 | 6/2015 | Anderson et al. |
| 9,084,465 B2 | 7/2015 | Oostman, Jr. et al. |
| 9,119,945 B2 | 9/2015 | Simons et al. |
| 9,439,673 B2 | 9/2016 | Austen |
| 9,561,051 B2 | 2/2017 | Austen et al. |
| D797,286 S | 9/2017 | Ginggen et al. |
| 2002/0022854 A1 | 2/2002 | Irion et al. |
| 2002/0022861 A1 | 2/2002 | Jacobs et al. |
| 2002/0045859 A1 | 4/2002 | Gartstein et al. |
| 2002/0103500 A1 | 8/2002 | Gildenberg |
| 2002/0120260 A1 | 8/2002 | Morris et al. |
| 2002/0169431 A1 | 11/2002 | Kline et al. |
| 2002/0183688 A1 | 12/2002 | Lastovich et al. |
| 2002/0188280 A1 | 12/2002 | Nguyen et al. |
| 2003/0023196 A1 | 1/2003 | Liguori |
| 2003/0088220 A1 | 5/2003 | Molander et al. |
| 2003/0119641 A1 | 6/2003 | Reising |
| 2003/0135161 A1 | 7/2003 | Fleming et al. |
| 2003/0158521 A1 | 8/2003 | Ameri |
| 2003/0158566 A1 | 8/2003 | Brett |
| 2003/0181936 A1 | 9/2003 | Trautman et al. |
| 2003/0195625 A1 | 10/2003 | Garcia Castro et al. |
| 2003/0199811 A1 | 10/2003 | Sage et al. |
| 2003/0233082 A1 | 12/2003 | Kline et al. |
| 2004/0002723 A1 | 1/2004 | Ball |
| 2004/0010268 A1 | 1/2004 | Gabehart |
| 2004/0015139 A1 | 1/2004 | La Bianco et al. |
| 2004/0023771 A1 | 2/2004 | Reising et al. |
| 2004/0054410 A1 | 3/2004 | Barrows |
| 2004/0073195 A1 | 4/2004 | Cucin |
| 2004/0122471 A1 | 6/2004 | Toby et al. |
| 2004/0162566 A1 | 8/2004 | Carson et al. |
| 2004/0175690 A1 | 9/2004 | Mishra et al. |
| 2004/0220589 A1 | 11/2004 | Feller |
| 2005/0049582 A1 | 3/2005 | DeBenedictis et al. |
| 2005/0090765 A1 | 4/2005 | Fisher |
| 2005/0130821 A1 | 6/2005 | Reising et al. |
| 2005/0165329 A1 | 7/2005 | Taylor et al. |
| 2005/0203575 A1 | 9/2005 | Carson et al. |
| 2005/0209567 A1 | 9/2005 | Sibbitt |
| 2005/0215921 A1 | 9/2005 | Hibner et al. |
| 2005/0215970 A1 | 9/2005 | Kline et al. |
| 2005/0215971 A1 | 9/2005 | Roe et al. |
| 2005/0226856 A1 | 10/2005 | Ahlfors |
| 2005/0234419 A1 | 10/2005 | Kline et al. |
| 2005/0245952 A1 | 11/2005 | Feller |
| 2005/0283141 A1 | 12/2005 | Giovannoli |
| 2006/0047234 A1 | 3/2006 | Glucksman et al. |
| 2006/0064031 A1 | 3/2006 | Miller |
| 2006/0116605 A1 | 6/2006 | Nakao |
| 2006/0155266 A1 | 7/2006 | Manstein et al. |
| 2006/0161179 A1 | 7/2006 | Kachenmeister |
| 2006/0184153 A1 | 8/2006 | Mark et al. |
| 2006/0216781 A1 | 9/2006 | Gebing |
| 2006/0259006 A1 | 11/2006 | McKay et al. |
| 2006/0264926 A1 | 11/2006 | Kochamba |
| 2006/0271070 A1 | 11/2006 | Eriksson et al. |
| 2007/0010810 A1 | 1/2007 | Kochamba |
| 2007/0038181 A1 | 2/2007 | Melamud et al. |
| 2007/0038236 A1 | 2/2007 | Cohen |
| 2007/0060888 A1 | 3/2007 | Goff et al. |

(56) References Cited

U.S. PATENT DOCUMENTS

| | | |
|---|---|---|
| 2007/0073217 A1 | 3/2007 | James |
| 2007/0073327 A1 | 3/2007 | Giovannoli |
| 2007/0078466 A1 | 4/2007 | Bodduluri et al. |
| 2007/0078473 A1 | 4/2007 | Bodduluri et al. |
| 2007/0106306 A1 | 5/2007 | Bodduluri et al. |
| 2007/0142722 A1 | 6/2007 | Chang |
| 2007/0142744 A1 | 6/2007 | Provencher |
| 2007/0142885 A1 | 6/2007 | Hantash et al. |
| 2007/0149991 A1 | 6/2007 | Mulholland |
| 2007/0156161 A1 | 7/2007 | Weadock et al. |
| 2007/0167958 A1 | 7/2007 | Sulamanidze et al. |
| 2007/0179455 A1 | 8/2007 | Geliebter et al. |
| 2007/0183938 A1 | 8/2007 | Booker |
| 2007/0198000 A1 | 8/2007 | Miyamoto et al. |
| 2007/0213634 A1 | 9/2007 | Teague |
| 2007/0239236 A1 | 10/2007 | Manstein |
| 2007/0239260 A1 | 10/2007 | Palanker et al. |
| 2007/0249960 A1 | 10/2007 | Williamson |
| 2007/0270710 A1 | 11/2007 | Frass et al. |
| 2008/0009802 A1 | 1/2008 | Lambino et al. |
| 2008/0009901 A1 | 1/2008 | Redmond et al. |
| 2008/0033334 A1 | 2/2008 | Gurtner et al. |
| 2008/0045858 A1 | 2/2008 | Tessitore et al. |
| 2008/0045861 A1 | 2/2008 | Miller et al. |
| 2008/0132979 A1 | 6/2008 | Gerber |
| 2008/0146982 A1 | 6/2008 | Rastegar et al. |
| 2008/0183167 A1 | 7/2008 | Britva et al. |
| 2008/0208146 A1 | 8/2008 | Brandwein et al. |
| 2008/0221548 A1 | 9/2008 | Danenberg et al. |
| 2008/0234602 A1 | 9/2008 | Oostman et al. |
| 2008/0234699 A1 | 9/2008 | Oostman, Jr. et al. |
| 2008/0275378 A1 | 11/2008 | Herndon |
| 2008/0300507 A1 | 12/2008 | Figueredo et al. |
| 2008/0306471 A1 | 12/2008 | Altshuler et al. |
| 2008/0312648 A1 | 12/2008 | Peterson |
| 2009/0030340 A1 | 1/2009 | Mc Clellan |
| 2009/0093864 A1 | 4/2009 | Anderson |
| 2009/0146068 A1 | 6/2009 | Agarwal |
| 2009/0198336 A1 | 8/2009 | Qiao et al. |
| 2009/0227895 A1 | 9/2009 | Goldenberg |
| 2009/0312749 A1 | 12/2009 | Pini et al. |
| 2010/0023003 A1 | 1/2010 | Mulholland |
| 2010/0041938 A1 | 2/2010 | Stoianovici et al. |
| 2010/0057100 A1 | 3/2010 | Zeevi |
| 2010/0082042 A1 | 4/2010 | Drews |
| 2010/0121307 A1 | 5/2010 | Lockard et al. |
| 2010/0145373 A1 | 6/2010 | Alon |
| 2010/0160822 A1 | 6/2010 | Parihar et al. |
| 2010/0185116 A1 | 7/2010 | Al-Mohizea |
| 2010/0330589 A1 | 12/2010 | Bahrami et al. |
| 2011/0009882 A1 | 1/2011 | Remsburg et al. |
| 2011/0028898 A1 | 2/2011 | Clark, III et al. |
| 2011/0092844 A1 | 4/2011 | Bargo et al. |
| 2011/0105949 A1 | 5/2011 | Wiksell |
| 2011/0152738 A1 | 6/2011 | Zepeda et al. |
| 2011/0172745 A1 | 7/2011 | Na et al. |
| 2011/0245834 A1 | 10/2011 | Miklosovic |
| 2011/0251602 A1 | 10/2011 | Anderson et al. |
| 2011/0282238 A1 | 11/2011 | Houser et al. |
| 2011/0313429 A1 | 12/2011 | Anderson et al. |
| 2012/0041430 A1 | 2/2012 | Anderson et al. |
| 2012/0065551 A1 | 3/2012 | Aviad et al. |
| 2012/0136387 A1 | 5/2012 | Redmond et al. |
| 2012/0158100 A1 | 6/2012 | Schomacker |
| 2012/0209283 A1 | 8/2012 | Zhu |
| 2012/0226214 A1 | 9/2012 | Gurtner et al. |
| 2012/0226268 A1 | 9/2012 | Liu et al. |
| 2012/0226306 A1 | 9/2012 | Jackson et al. |
| 2012/0245629 A1 | 9/2012 | Gross et al. |
| 2012/0253333 A1 | 10/2012 | Garden et al. |
| 2012/0271320 A1 | 10/2012 | Hall et al. |
| 2013/0006168 A1 | 1/2013 | Del Vecchio |
| 2013/0045171 A1 | 2/2013 | Utecht et al. |
| 2013/0110026 A1 | 5/2013 | Jackson et al. |
| 2013/0131635 A1 | 5/2013 | Rimsa et al. |
| 2013/0204238 A1 | 8/2013 | Lederman et al. |
| 2014/0036523 A1 | 2/2014 | Thullier et al. |
| 2014/0039523 A1 | 2/2014 | Austen |
| 2014/0163582 A1 | 6/2014 | Austen et al. |
| 2014/0200484 A1 | 7/2014 | Austen et al. |
| 2014/0277055 A1 | 9/2014 | Austen, Jr. |
| 2014/0296741 A1 | 10/2014 | Austen |
| 2014/0296796 A1 | 10/2014 | Lim |
| 2014/0303648 A1 | 10/2014 | Knowlton |
| 2015/0143713 A1 | 5/2015 | Cheng |
| 2015/0173991 A1 | 6/2015 | Anderson et al. |
| 2015/0238214 A1 | 8/2015 | Anderson et al. |
| 2015/0258319 A1 | 9/2015 | Simmers |
| 2015/0320990 A1 | 11/2015 | Burton et al. |
| 2015/0366719 A1 | 12/2015 | Levinson et al. |
| 2016/0082241 A1 | 3/2016 | Burton et al. |
| 2016/0095592 A1 | 4/2016 | Levinson et al. |
| 2016/0121091 A1 | 5/2016 | Burton et al. |
| 2016/0136406 A1 | 5/2016 | Berry et al. |
| 2016/0192961 A1 | 7/2016 | Ginggen et al. |
| 2016/0317721 A1 | 11/2016 | Ginggen et al. |
| 2016/0367280 A1 | 12/2016 | Austen |
| 2017/0367729 A1 | 12/2017 | Ginggen et al. |
| 2018/0008500 A1 | 1/2018 | Anderson et al. |
| 2018/0021087 A1 | 1/2018 | Anderson et al. |
| 2018/0078278 A1 | 3/2018 | Levinson et al. |
| 2018/0193054 A1 | 7/2018 | Austen |
| 2018/0206875 A1 | 7/2018 | Austen et al. |

FOREIGN PATENT DOCUMENTS

| | | |
|---|---|---|
| CN | 2126570 Y | 1/1993 |
| CN | 1115629 A | 1/1996 |
| CN | 201005966 Y | 1/2008 |
| CN | 101128156 A | 2/2008 |
| CN | 101208128 A | 6/2008 |
| CN | 101232858 A | 7/2008 |
| CN | 101277657 A | 10/2008 |
| CN | 101312692 A | 11/2008 |
| CN | 101347346 A | 1/2009 |
| CN | 101670145 A | 3/2010 |
| CN | 202113484 U | 1/2012 |
| CN | 103547226 A | 1/2014 |
| DE | 287651 A5 | 3/1991 |
| DE | 202004010659 U1 | 10/2004 |
| DE | 102007026973 A1 | 12/2008 |
| EP | 0027974 A1 | 5/1981 |
| EP | 1224949 A1 | 7/2002 |
| EP | 1278061 A1 | 1/2003 |
| EP | 1396230 A1 | 3/2004 |
| EP | 2181732 A1 | 5/2010 |
| EP | 1278061 B1 | 2/2011 |
| EP | 2409727 A1 | 1/2012 |
| FR | 2846221 B1 | 7/2005 |
| JP | S57-163208 A | 10/1982 |
| JP | 2000-139929 A | 5/2000 |
| JP | 2001-187058 A | 7/2001 |
| JP | 2002-505605 A | 2/2002 |
| JP | 2003-515424 A | 5/2003 |
| JP | 2003-532480 A | 11/2003 |
| JP | 2004-503342 A | 2/2004 |
| JP | 2005-000642 A | 1/2005 |
| JP | 2005-103276 A | 4/2005 |
| JP | 2006-516201 A | 6/2006 |
| JP | 2006-517814 A | 8/2006 |
| JP | 2007-041267 A | 2/2007 |
| JP | 2007-100140 A | 4/2007 |
| JP | 2008-036393 A | 2/2008 |
| JP | 2008-528207 A | 7/2008 |
| JP | 2009-507773 A | 2/2009 |
| JP | 2009-509671 A | 3/2009 |
| JP | 2009-172418 A | 8/2009 |
| JP | 2009-219858 A | 10/2009 |
| JP | 2009-545382 A | 12/2009 |
| JP | 2010-000210 A | 1/2010 |
| JP | 4431637 B2 | 3/2010 |
| JP | 2010-515469 A | 5/2010 |
| JP | 2010-525887 A | 7/2010 |
| JP | 2010-532178 A | 10/2010 |

(56) References Cited

FOREIGN PATENT DOCUMENTS

| | | |
|---|---|---|
| JP | 2011-516169 A | 5/2011 |
| JP | 5944925 B2 | 7/2016 |
| KR | 2008-0030553 A | 4/2008 |
| KR | 2008-0049793 A | 6/2008 |
| KR | 2010-0135863 A | 12/2010 |
| KR | 2010/0135864 A | 12/2010 |
| RU | 1801391 C | 3/1993 |
| RU | 2119304 C1 | 9/1998 |
| RU | 58359 U1 | 11/2006 |
| RU | 2289332 C2 | 12/2006 |
| RU | 2308873 C2 | 10/2007 |
| RU | 2325859 C2 | 6/2008 |
| TW | 402497 B | 8/2000 |
| TW | 200841866 A | 11/2008 |
| WO | WO-93/22971 A1 | 11/1993 |
| WO | WO-1995/28896 A1 | 11/1995 |
| WO | WO-97/18758 A1 | 5/1997 |
| WO | WO-98/26719 A1 | 6/1998 |
| WO | WO-98/57587 A1 | 12/1998 |
| WO | WO-99/29243 A1 | 6/1999 |
| WO | WO-0141651 A2 | 6/2001 |
| WO | WO-01/85035 A2 | 11/2001 |
| WO | WO-02/05890 A2 | 1/2002 |
| WO | WO-02/096321 A1 | 12/2002 |
| WO | WO-2004/045671 A2 | 6/2004 |
| WO | WO-2005/013830 A1 | 2/2005 |
| WO | WO-2005/072181 A2 | 8/2005 |
| WO | WO-2005/109799 A2 | 11/2005 |
| WO | WO-2006/081556 A2 | 8/2006 |
| WO | WO-2006/116281 A2 | 11/2006 |
| WO | WO-2006/118804 A1 | 11/2006 |
| WO | WO-2007/011788 A2 | 1/2007 |
| WO | WO-2007/015232 A1 | 2/2007 |
| WO | WO-2007/024038 A1 | 3/2007 |
| WO | WO-2007/041267 A2 | 4/2007 |
| WO | WO-2007/080596 A2 | 7/2007 |
| WO | WO-2007/106170 A2 | 9/2007 |
| WO | WO-2008/019051 A2 | 2/2008 |
| WO | WO-2008/033873 A2 | 3/2008 |
| WO | WO-2008/052189 A2 | 5/2008 |
| WO | WO-2009/040493 A1 | 4/2009 |
| WO | WO-2009/072711 A2 | 6/2009 |
| WO | WO-2009/099988 A2 | 8/2009 |
| WO | WO-2009/137288 A2 | 11/2009 |
| WO | WO-2009/146053 A1 | 12/2009 |
| WO | WO-2009/146068 A1 | 12/2009 |
| WO | WO-2009/146072 A1 | 12/2009 |
| WO | WO-2010/027188 A2 | 3/2010 |
| WO | WO-2010/080014 A2 | 7/2010 |
| WO | WO-2010/097790 A1 | 9/2010 |
| WO | WO-2011/006009 A1 | 1/2011 |
| WO | WO-2011/019859 A2 | 2/2011 |
| WO | WO-2011/075676 A2 | 6/2011 |
| WO | WO-2011/075676 A3 | 11/2011 |
| WO | WO-2011140497 A2 | 11/2011 |
| WO | WO-2012/052986 A2 | 4/2012 |
| WO | WO-2012/103483 A2 | 8/2012 |
| WO | WO-2012/103488 A1 | 8/2012 |
| WO | WO-2012/103492 A1 | 8/2012 |
| WO | WO-2012/119131 A1 | 9/2012 |
| WO | WO-2012/135828 A1 | 10/2012 |
| WO | WO-2013/013196 A1 | 1/2013 |
| WO | WO-2013/013199 A2 | 1/2013 |
| WO | WO-2014/008470 A1 | 1/2014 |
| WO | WO-2014/089488 A2 | 6/2014 |
| WO | WO-2014/130359 A1 | 8/2014 |
| WO | WO-2014/151104 A1 | 9/2014 |
| WO | WO-2014/179729 A1 | 11/2014 |
| WO | WO-2015/021434 A2 | 2/2015 |
| WO | WO-2015/051164 A2 | 4/2015 |
| WO | WO-2015/095675 A1 | 6/2015 |
| WO | WO-2015/126926 A1 | 8/2015 |
| WO | WO-2016/033584 A1 | 3/2016 |
| WO | WO-2016/033586 A1 | 3/2016 |
| WO | WO-2016/077759 A1 | 5/2016 |
| WO | WO-2016/127091 A1 | 8/2016 |
| WO | WO-2017/139773 A2 | 8/2017 |
| WO | WO-2017/172920 A1 | 10/2017 |
| WO | WO-2017/192723 A1 | 11/2017 |
| WO | WO-2018/057630 A1 | 3/2018 |
| WO | WO-2018/057637 A1 | 3/2018 |

OTHER PUBLICATIONS

Banzhaf, C. et al., Spatiotemporal Closure of Fractional Laser-Ablated Channels Imaged by Optical Coherence Tomography and Reflectance Confocal Microscopy, Lasers in Surgery and Medicine, 48:157-165 (2016).
Bedi, V. et al., The effects of pulse energy variations on the dimensions of microscopic thermal treatment zones in nonablative fractional resurfacinq, Lasers Surg Med, 39(2):145-55 (2007).
Cevc, Gregor, Drug delivery across the skin, Expert Opinion Investigational Drugs, 6(12):1887-937 (1997).
Chang, Te-Sheng, An updated review of tyrosinase inhibitors, Int J Mol Sci, 10(6):2440-2475 (2009).
International Search Report for International Patent Application No. PCT/US2012/022980 dated Aug. 9, 2012.
International Written Opinion for International Patent Application No. PCT/US2012/022980 dated Aug. 9, 2012.
Czech, Z. et al., Pressure-sensitive adhesives for medical applications, Wide Spectra of Quality Control, Akyar, 309-332 (2011).
de las Heras Alarcon et al., Stimuli responsive polymers for biomedical applications, Chem Soc Rev. 34(3):276-85 (2005).
Dini, G. et al., Grasping leather plies by Bernoulli grippers, CIRP Ann Manuf Technol. 58(1):21-4 (2009).
Dujardin, J. et al., In vivo assessment of skin electroporation using square wave pulses, J Control Release, 79(1-3):219-27 (2002).
Dunkin, C. et al., Scarring occurs at a critical depth of skin injury: precise measurement in a graduated dermal scratch in human volunteers, Plast Reconstr Surg, 119(6):1722-32 (2007).
European Patent Office, Supplementary European Search Report, Application No. EP13813955.5, dated Mar. 18, 2016.
European Search Report for European Application No. 12739664.6 dated May 20, 2014.
Extended European Search Report, Application No. 12814711.3, dated Feb. 11, 2015.
Fernandes, J. et al., Micro-mechanical fractional skin rejuvenation, Plast Reconstr Surg, 130(5S-1):28 (2012).
Fernandes, J. et al., Micro-mechanical fractional skin rejuvenation, Plast Reconstr Surg, 131(2):216-23 (2013).
Galaev., 'Smart' polymers in biotechnology and medicine, Russ Chem Rev. 64(5):471-489 (1995).
Hale, G. and Querry, M., Optical constants of water in the 200-nm to 200-microm wavelength region, Appl Opt, 12(3):555-63 (1973).
Han, H. et al., Combined, Minimally Invasive, Thread-based Facelift, Archives of Aesthetic Plastic Surgery, 20(3):160-164 (2014).
Huang, W.M. et al., Shape memory materials, Material Today, 13(7-8):54-61 (2010).
International Preliminary Report on Patentability for International Patent Application No. PCT/US2009/039125, dated Oct. 5, 2010 (6 pages).
International Preliminary Report on Patentability for International Patent Application No. PCT/US2012/022987, dated Jul. 30, 2013 (5 pages).
International Preliminary Report on Patentability for International Patent Application No. PCT/US2012/022993, dated Jul. 30, 2013 (5 pages).
International Preliminary Report on Patentability for International Patent Application No. PCT/US2012/047716, dated Nov. 4, 2014 (4 pages).
International Preliminary Report on Patentability for International Patent Application No. PCT/US2013/049445, dated Jan. 6, 2015 (4 pages).
International Preliminary Report on Patentability for International Patent Application No. PCT/US2014/036638, dated Nov. 3, 2015 (7 pages).

(56) References Cited

OTHER PUBLICATIONS

International Preliminary Report on Patentability for International Patent Application No. PCT/US2014/050426, dated Feb. 9, 2016 (8 pages).
International Search Report and Written Opinion for International Patent Application No. PCT/US2009/039125, dated Nov. 16, 2009 (9 pages).
International Search Report and Written Opinion for International Patent Application No. PCT/US2012/022987, dated Apr. 12, 2012 (6 pages).
International Search Report and Written Opinion for International Patent Application No. PCT/US2012/022993, dated May 17, 2012 (6 pages).
International Search Report and Written Opinion for International Patent Application No. PCT/US2012/047716, dated Oct. 25, 2012 (5 pages).
International Search Report and Written Opinion for International Patent Application No. PCT/US2013/049445, dated Oct. 18, 2013 (5 pages).
International Search Report and Written Opinion for International Patent Application No. PCT/US2014/016483, dated May 6, 2014 (9 pages).
International Search Report and Written Opinion for International Patent Application No. PCT/US2014/036638, dated Oct. 2, 2014 (10 pages).
International Search Report and Written Opinion for International Patent Application No. PCT/US2014/050426, dated Feb. 4, 2015 (11 pages).
International Search Report and Written Opinion for PCT/US2009/039125 dated Nov. 16, 2009.
International Search Report and Written Opinion for PCT/US2011/035613, dated May 6, 2011.
International Search Report and Written Opinion issued by the Korean Intellectual Property Office as International Searching Authority for International Application No. PCT/US2009/039114 dated Nov. 16, 2009 (10 pages).
International Search Report and Written Opinion under dated Oct. 18, 2013 in connection with PCT/US2013/049445.
International Search Report for International Patent Application No. PCT/US2012/022993 dated May 17, 2012.
International Search Report for International Patent Application No. PCT/US2012/047708.
International Search Report for PCT/US14/71443, 3 pages (dated Mar. 19, 2015).
International Search Report for PCT/US2014/016483, 3 pages (dated May 6, 2014).
International Search Report for PCT/US2015/060685, 3 pages (dated Feb. 2, 2016).
International Search Report for PCT/US2017/024752, 8 pages (dated Aug. 29, 2017).
International Search Report for PCT/US2017/052528 (Devices and Methods for Cosmetic Skin Resurfacing, filed Sep. 20, 2017), issued by ISA/US, 5 pages (dated Jan. 4, 2018).
International Search Report for PCT/US2017/052539 (Rapid Skin Treatment Using Microcoring, filed Sep. 20, 2017), issued by ISA/US, 7 pages (dated Nov. 22, 2017).
International Searching Report and Written Opinion issued by the Korean Intellectual Property Office as International Search Authority for International Application No. PCT/US2011/035613 dated Jan. 12, 2012 (6 pages).
International Written Opinion for International Patent Application No. PCT/US2012/022993 dated May 17, 2012.
International Written Opinion or International Patent Application No. PCT/US2012/022987 dated Apr. 12, 2012.
Kakasheva-Mazenkovska, L. et al., Variations of the histomorphological characteristics of human skin of different body regions in subjects of different age, Contributions, 32(2):119-28 (2011).
Konermann, W. et al., Ultrasonographically guided needle biopsy of benign and malignant soft tissue and bone tumors, J Ultrasound Med, 19(7):465-71 (2000).
Lien, T.K. and Davis, P.G.G., A novel gripper for limp materials based on lateral Coanda ejectors, CIRP Ann Manuf Technol, 57(1):33-6 (2008).
Majid, Imran, Microneedling therapy in atrophic facial scars: an objective assessment, J Cutan Aesthet Surg. 2(1):26-30 (2009).
Moore, J. et al., Modeling of the Plane Needle Cutting Edge Rake and Inclination Angles for Biopsy, Journal of Manufacturing Science and Engineering, 132:051005-1-051005-8 (2010).
PCT International Preliminary Report on Patentability, PCT/US2014/036638, dated Nov. 3, 2015, 7 pages.
PCT International Preliminary Report on Patentability, PCT/US2014/050426, dated Feb. 9, 2016, 8 pages.
PCT International Search Report and Written Opinion, PCT/US2014/036638, dated Oct. 2, 2014, 10 pages.
PCT International Search Report and Written Opinion, PCT/US2014/050426, dated Feb. 4, 2015, 18 pages.
Pliquett, U. et al., A propagating heat wave model of skin electroporation, J Theor Biol, 251(2):195-201 (2008).
Prausnitz, M. et al., Electroporation of mammalian skin: a mechanism to enhance transdermal drug delivery, Proc Natl Acad Sci USA, 90(22):10504-8 (1993).
Salam, G. and Amin, J., The basic Z-plasty, Am Fam Physician, 67(11):2329-32 (2003).
Written Opinion for International Patent Application No. PCT/US2012/047708.
Written Opinion for PCT/US14/71443, 4 pages (dated Mar. 19, 2015).
Written Opinion for PCT/US2014/016483, 6 pages (dated May 6, 2014).
Written Opinion for PCT/US2015/060685, 4 pages (dated Feb. 2, 2016).
Written Opinion for PCT/US2017/024752, 11 pages (dated Aug. 29, 2017).
Written Opinion for PCT/US2017/052528 (Devices and Methods for Cosmetic Skin Resurfacing, filed Sep. 20, 2017), issued by ISA/US, 17 pages (dated Jan. 4, 2018).
Written Opinion for PCT/US2017/052539 (Rapid Skin Treatment Using Microcoring, filed Sep. 20, 2017), issued by ISA/US, 8 pages (dated Nov. 22, 2017).
Zhu, J. et al., The Efficacy and Safety of Fractional CO2 Laser Combined with Topical Type A Botulinum Toxin for Facial Rejuvenation: A Randomized Controlled Split-Face Study, BioMed Research International, 7 pages (2016).
Lemperle, G. et al., A Classification of Facial Wrinkles, Plastic and Reconstructive Surgery, 108(6):1735-1750 (2001).
Narins, R. et al., Validated Assessment Scales for the Lower Face, Dermatology Surgery, 38:333-342 (2012).

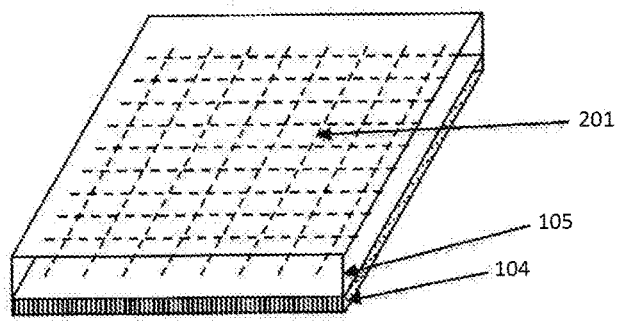
Figure 2
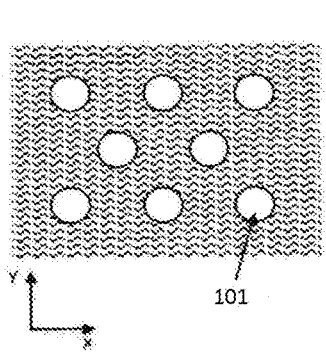 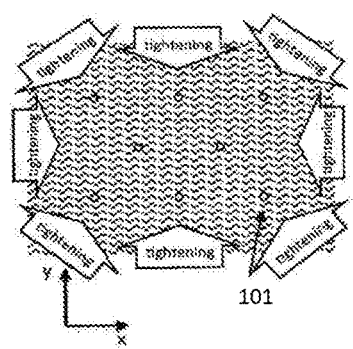 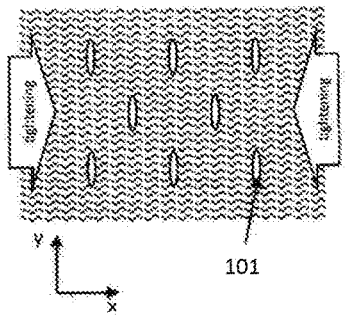
Figure 3A          Figure 3B          Figure 3C

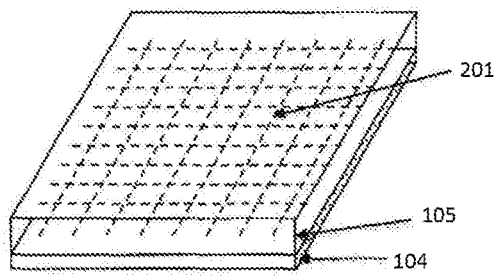
Figure 4A
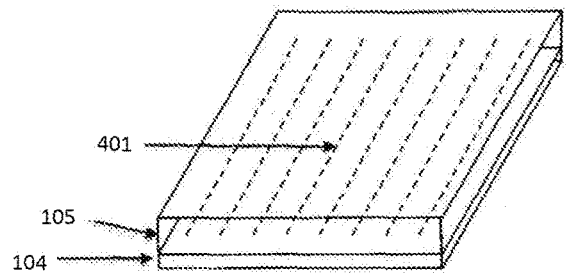
Figure 4B
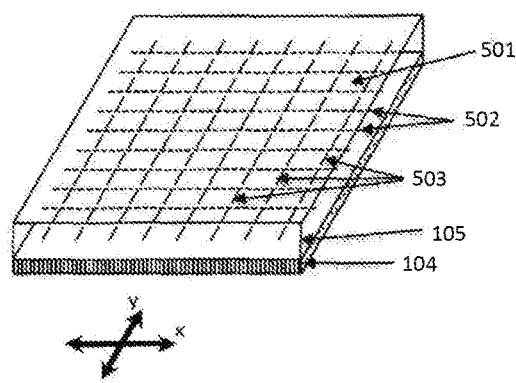
Figure 5

METHODS AND DEVICES FOR SKIN TIGHTENING

CROSS-REFERENCE TO RELATED APPLICATIONS

This application is a continuation application of U.S. application Ser. No. 14/764,866, filed on Jul. 30, 2015, which is a U.S. National Phase Application under 35 U.S.C. § 371 of International Patent Application No. PCT/US2014/016483, filed on Feb. 14, 2014, which claims benefit of U.S. Provisional Application No. 61/766,937, filed Feb. 20, 2013, the contents of each of which are hereby incorporated by reference in their entirety.

BACKGROUND OF THE INVENTION

This invention relates to methods and devices for skin tightening or for treating diseases, disorders, and conditions that would benefit from skin restoration or tightening.

Many human health issues arise from the damage or loss of tissue due to disease, advanced age, and/or injury. In aesthetic medicine, elimination of excess tissue and/or skin laxity is an important concern that affects more than 25% of the U.S. population. Conventional surgical therapies (e.g., a face lift, brow lift, or breast lift) can be effective but are often invasive, inconvenient, and expensive, while scarring limits its applicability.

Although minimally invasive methods are available, such methods are generally less effective than surgical methods. Methods using energy sources (e.g., laser, non-coherent light, radiofrequency, or ultrasound) can be effective at improving the architecture and the texture of the skin but are much less effective at tightening the skin or reducing skin laxity. Neurotoxins, such as botulinum toxin, reduce the formation of dynamic wrinkles by paralysis of the injected muscles, but such toxins have minimal or no effect on skin tightness or laxity. Finally, dermal fillers, such as hyaluronic acid, are injected in the dermal layer to smooth out wrinkles and improve contours, but such fillers do not tighten or reduce laxity of the skin. Thus, surgical therapies remain the gold standard for lifting and/or tightening skin, as compared to energy-based techniques (e.g., with laser, radiofrequency, or ultrasound ablation) and injection-based techniques (e.g., with botulinum toxin or hyaluronic acid- or collagen-based fillers).

Accordingly, there is a need for improved methods and devices that increase the effectiveness of minimally-invasive techniques while maintaining convenience, affordability, and/or accessibility to patients requiring tissue restoration.

SUMMARY OF THE INVENTION

This invention relates to methods and devices (e.g., a dressing) for the tightening of skin (or the reduction of skin laxity) by selective opening or closing a plurality of small slits or holes (e.g., wounds) formed by incision or excision of tissue portions. For example, tissue excision can be performed by fractional ablation of the epidermal and/or dermal layer of the skin with a hollow coring needle, by fractional laser ablation, by fractional radiofrequency ablation, or by fractional ultrasonic ablation. Various methods and devices are provided to close small wounds, including smart or tunable dressings that allow for titration of the tightening effect after application to the skin of a subject.

Accordingly, the present invention features a tunable dressing including (i) an adhesive layer and (ii) a regulatable layer that includes one or more materials, where exposure of the regulatable layer to one or more external stimuli (e.g., any described herein) results in a change in a physical characteristic (e.g., any described herein) in the one or more materials in at least a portion of the dressing (e.g., including planar or non-planar changes across the entire device or in a portion of the device).

The present invention also features a tunable dressing including (i) an adhesive layer and (ii) an unstretched layer that includes one or more materials, where exposure of the unstretched layer to one or more external stimuli (e.g., any described herein) results in contraction or expansion in one or more directions (e.g., in the x-, y-, z-, xy-, xz-, yz-, and/or xyz-directions) in at least a portion of the area of the dressing. In some embodiments, the contraction or expansion is in the x-axis, y-axis, and/or z-axis of the dressing, as compared to before the exposure (e.g., in the xy-, xz-, yz-, and/or xyz-plane of the dressing, as compared to before the exposure). In further embodiments, the contraction or expansion is uniform or non-uniform.

In some embodiments, the change in a physical characteristic includes an increase in tension of the dressing, a decrease in tension of the dressing, an increase in compressive force exerted by the dressing, a decrease in compressive force exerted by the dressing, compression in one or more directions of the dressing, and/or expansion in one or more directions of the dressing (e.g., where such an increase or decrease is in the x-axis, y-axis, and/or z-axis or in the xy-, xz-, xy-, and/or xyz-plane of the dressing, as compared to before the exposure). In particular embodiments, the increase or decrease in tension or compressive force and/or the expansion or compression of the device is an increase or decrease of intensity of at least about 0.5% after exposure of the one or more external stimuli, as compared to before the exposure (e.g., an increase or decrease of at least about 0.5% (e.g., at least about 0.6%, 0.7%, 0.8%, 0.9%, 1.0%, 1.1%, 1.2%, 1.5%, 1.7%, 2.0%, 2.2%, 2.5%, 2.7%, 3%, 3.5%, 4%, 4.5%, 5%, 5.5%, 6%, 6.5%, 7%, 7.5%, 8%, 8.5%, 9%, 9.5%, 10%, 10.5%, 15%, 20%, 30%, 35%, 40%, 45%, 50%, 55%, 60%, or more) or from about 0.5% to 20%, 20% to 30%, 30% to 40%, 30% to 50%, or 50% to 60%). In some embodiments, the physical characteristic is one or more of compression, expansion, tension, structure, size, porosity, surface chemistry, bending modulus, fracture or failure strain, resilience, permeability, swelling ratio, elasticity, electric conductivity, plasticity, resilience, resistance (e.g., creep resistance), strength (e.g., as measured by Young's modulus, tensile strength, compressive strength, impact strength, or yield strength), stress (e.g., compressive stress, shear stress, or tensile stress), load, and/or strain (e.g., as measured by deflection, deformation, strain at failure, or ultimate strain).

In any embodiment described herein, the change in a physical characteristic occurs in a portion of the dressing or across the entire dressing. In other embodiments, the change in a physical characteristic is non-uniform across the entire dressing or in a portion of the dressing. In yet other embodiments, the change in a physical characteristic is uniform across the entire dressing or in a portion of the dressing.

In any of the devices, dressings, apparatuses, and methods described herein, the one or more materials are configured in a random, non-geometric, and/or geometric arrangement to provide contraction and/or expansion in one or more directions in at least a portion of the area of the dressing. In particular embodiments, the arrangement is geometric (e.g., a uniform or non-uniform arrangement). In some embodiments, the geometric arrangement includes a first material arranged in a first direction and optionally a second material arranged in a second direction (e.g., where the second direction is approximately orthogonal to the first direction). In further embodiments, each of the first material or the second material is, independently, a shape-memory polymer, a shape-memory alloy, a thermal-responsive material, a pH-responsive material, a light-responsive material, a moisture-responsive material, a solvent-responsive or chemical exposure-responsive material, an electric field-responsive material, a magnetic field-responsive material, an actuator-embedded material, or an unstretched material (e.g., any described herein).

In any of the devices, dressings, apparatuses, and methods described herein, the one or more external stimuli is, independently, a change in temperature, pH, light, moisture, solvent, chemical exposure, electric field, and/or magnetic field (e.g., which can optionally result in mechanical, hydraulic, and/or pneumatic tuning).

In any embodiment described herein, exposure of the device (e.g., dressing or a layer of the device, as well as portions thereof) to two or more external stimuli (e.g., three, four, five, six, seven, eight, nine, ten, or more external stimuli) results in a change in two or more physical characteristics (e.g., three, four, five, six, seven, eight, nine, ten, or more changes in physical characteristics).

In any embodiment described herein, the regulatable layer or the unstretched layer includes two or more materials (e.g., three, four, five, six, seven, eight, nine, ten, or more materials). In particular embodiments, at least one of the materials (e.g., at least two, three, four, five, or more in one, two, three, four, or more layers) is a stimulus-responsive material (e.g., any described herein). Exemplary materials include a shape-memory polymer (e.g., including shape-memory polyurethane; block copolymers including poly(ethylene terephthalate), polystyrene, polyethylene glycol, poly(1,4-butadiene), polynorbornene, polyacrylate, and/or polyurethane, as well as shape-memory composites and shape-memory hybrids), a shape-memory alloy (e.g., any alloy described herein, such as a NiTi alloy), a thermal-responsive material (e.g., any such material described herein, such as polymers including poly-N-isopropylacrylam ide, poly-N-vinylcaprolactam, poly-N,N-diethylacrylamide, and/or a polyalkylacrylamide), a pH-responsive material (e.g., any described herein, such as polymers and copolymers including one or more polyacrylic acid, polymethacrylic acid, methacrylic acid/methyl methacrylate, and carboxylic derivatives of any monomer described herein), a light-responsive material (e.g., a polymer including one or more light-responsive switches, as described herein), a moisture-responsive material (e.g., a polymer including one or more ionic monomers, as described herein), a solvent-responsive or chemical exposure-responsive material (e.g., a polymer composite, as described herein), an electric field-responsive material (e.g., a polymer including one or more electric field-responsive switches, as described herein), a magnetic field-responsive material (e.g., a polymer including one or more magnetic field-responsive switches, as described herein), an actuator-embedded material (e.g., a material including one or more MEMS actuators, carbon nanotubes, piezoceramic actuators (e.g., optionally having one or more interdigitated electrodes), multilayered actuators, optical fibers, piezopolymeric films, piezoplates, piezofibers, shape-memory polymers, or shape-memory alloys). In other embodiments, at least one of the materials (e.g., at least two, three, four, five, or more in one, two, three, four, or more layers) is a conventional material and/or a rigid material (e.g., any described herein, such as alginate, benzyl hyaluronate, carboxymethylcellulose, cellulose acetate, chitosan, collagen, dextran, epoxy, gelatin, hyaluronic acid, hydrocolloids, nylon (e.g., nylon 6 or PA6), pectin, poly (3-hydroxyl butyrate-co-poly (3-hydroxyl valerate), polyacrylate (PA), polyacrylonitrile (PAN), polybenzimidazole (PBI), polycarbonate (PC), polycaprolactone (PCL), polyester (PE), polyethylene glycol (PEG), polyethylene oxide (PEO), PEO/polycarbonate/polyurethane (PEO/PC/PU), poly(ethylene-co-vinyl acetate) (PEVA), PEVA/polylactic acid (PEVA/PLA), poly (ethylene terephthalate) (PET), PET/poly (ethylene naphthalate) (PET/PEN) polyglactin, polyglycolic acid (PGA), polyglycolic acid/polylactic acid (PGA/PLA), polyimide (PI), polylactic acid (PLA), poly-L-lactide (PLLA), PLLA/PC/polyvinylcarbazole (PLLA/PC/PVCB), poly ((3-malic acid)-copolymers (PMLA), polymethacrylate (PMA), poly (methyl methacrylate) (PMMA), polystyrene (PS), polyurethane (PU), poly (vinyl alcohol) (PVA), polyvinylcarbazole (PVCB), polyvinyl chloride (PVC), polyvinylidenedifluoride (PVDF), polyvinylpyrrolidone (PVP), silicone, rayon, or combinations thereof).

In any embodiment described herein, the dressing is tunable without removal of a portion of the dressing (e.g., without removal of one or more layers of the dressing). In any embodiment described herein, the adhesive layer includes a continuous layer of one or more adhesive materials or a discontinuous layer of one or more adhesive materials. In further embodiments, the discontinuous layer includes one or more adhesive materials in a random, geometric, or non-geometric arrangement (e.g., an array of one or more adhesive materials). In particular embodiments, the adhesive layer is tunable (e.g., results in a change in a physical characteristic in the one or more adhesive materials in at least a portion of the dressing or across the entire dressing). Exemplary adhesive materials include any described herein, such as a biodegradable adhesive; a pressure sensitive adhesive (e.g., a natural rubber, synthetic rubber (e.g., a styrene-butadiene or styrene-ethylene copolymer), polyvinyl ether, polyurethane, acrylic, silicone, or a ethylene-vinyl acetate copolymer); a biocompatible matrix (e.g., collagen (e.g., a collagen sponge), low melting agarose (LMA), polylactic acid (PLA), and/or hyaluronic acid (e.g., hyaluranon)); a photosensitizer (e.g., Rose Bengal, riboflavin-5-phosphate (R-5-P), methylene blue (MB), N-hydroxypyridine-2-(1H)-thione (N-HTP), a porphyrin, or a chlorin, as well as precursors thereof); a photochemical agent (e.g., 1,8 naphthalimide); a synthetic glue (e.g., a cyanoacrylate adhesive, a polyethylene glycol adhesive, or a gelatin-resorcinol-formaldehyde adhesive); or a biologic sealant (e.g., a mixture of riboflavin-5-phosphate and fibrinogen, a fibrin-based sealant, an albumin-based sealant, or a starch-based sealant).

In any embodiment described herein, the devices, apparatuses, dressings, and/or methods include one or more therapeutic agents selected from growth factors, analgesics (e.g., an NSAID, a COX-2 inhibitor, an opioid, a glucocorticoid agent, a steroid, or a mineralocorticoid agent, or any described herein), antibiotics, antifungals, anti-inflammatory agents, antimicrobials (e.g., chlorhexidine-, iodine-, or silver-based agents, as described herein), antiseptics (e.g., an alcohol, a quaternary ammonium compound, or any described herein), antiproliferative agents, steroids (for example, steroids to prevent edema), agents which prevent post-inflammatory skin hyperpigmentation (e.g., hydroquinone, azelaic acid, kojic acid, mandelic acid, or niacinamide), emollients, hemostatic agents, procoagulative agents, anticoagulative agents, immune modulators, proteins, or vitamins. In particular embodiments, the therapeutic agent is a hemostatic agent, a procoagulative agent, an anticoagulative agent, or combinations thereof. In some embodiments, the therapeutic agent is selected from the group of anhydrous aluminum sulfate, anti-fibrinolytic agent(s) (e.g., epsilon aminocaproic acid, tranexamic acid, or the like), anti-platelet agent(s) (e.g., aspirin, dipyridamole, ticlopidine, clopidogrel, or prasugrel), calcium alginate, cellulose, chitosan, coagulation factor(s) (e.g., II, V, VII, VIII, IX, X, XI, XIII, or Von Willebrand factor, as well as activated forms thereof), collagen (e.g., microfibrillar collagen), coumarin derivative(s) or vitamin K antagonist(s) (e.g., warfarin (coumadin), acenocoumarol, atromentin, phenindione, or phenprocoumon), desmopressin, epinephrine, factor Xa inhibitor(s) (e.g., apixaban or rivaroxaban), fibrinogen, heparin or derivatives thereof (e.g., low molecular weight heparin, fondaparinux, or idraparinux), poly-N-acetyl glucosamine, potassium alum, propyl gallate, silver nitrate, thrombin, thrombin inhibitor(s) (e.g., argatroban, bivalirudin, dabigatran, hirudin, lepirudin, or ximelagatran), titanium oxide, or a zeolite (e.g., a calcium-loaded zeolite).

The tunable dressings of the invention may also include moisturizers, emollients, ointments (including occlusive ointments and non-occlusive ointments), lotions, or creams, which may, if desired, provide a liquid or vapor barrier. Ingredients typically found in these materials include petrolatum, lanolin, glycerin, panthenol, paraffin, microcrystalline wax, ceresine, wool fat, bees wax, emulsifying wax, ceremide, and vegetable oils (e.g., olive, peanut, or coconut oil).

The present invention features a kit including: (a) a tunable dressing (e.g., any described herein) and (b) an applicator, where the applicator is configured for positioning the dressing on a skin region. In some embodiments, the applicator includes a frame or any structure configured to affix a dressing to the skin region (e.g., a disposable frame or a disposable structure). In some embodiments, the applicator holds the dressing to allow for aligning, positioning, and/or placing the dressing on the desired skin region. In yet other embodiments, the applicator is configured to allow for affixing a tunable dressing immediately after or shortly after forming one or more incisions or excisions in the skin region (e.g., within about 30 seconds, as described herein). In other embodiments, the kit includes a mechanical ablation device.

The present invention also features a kit including: (a) a tunable dressing (e.g., any described herein) and (b) an apparatus for making incisions and/or excisions in a skin region (e.g., a microablation tool, such as a fractional laser microablation tool, a fractional radiofrequency microablation tool, or a fractional ultrasonic microablation tool). In some embodiments, the kit further includes an applicator (e.g., any described herein), where the applicator is structurally configured to attach to the apparatus for making one or more incisions and/or excisions and to release a device (e.g., a tunable dressing) after making such an incision or excision.

In further embodiments, any of the kits described herein can include one or more of instructions on how to use the device(s), an air blower, a skin cooling device (e.g., cold air blower, Zimmer cooler, cold plate or other cold surface applied to the skin, cold gas, or cold liquid), a heat gun, a heating pad, one or more therapeutic agents (e.g., any described herein, such as an anticoagulative and/or procoagulative agent, and optionally in combination with a useful dispenser for applying the therapeutic agent, such as a brush, spray, film, ointment, cream, lotion, or gel), one or more wound cleansers (e.g., including any antibiotic, antimicrobial, or antiseptic, such as those described herein, in any useful form, such as a brush, spray, film, ointment, cream, lotion, or gel), one or more debriding agents, and/or other suitable or useful materials.

The present invention features methods of skin tightening including: (i) affixing a device to a skin region, where the skin region includes a plurality of incised tissue portions and/or excised tissue portions (for example, where at least two of the tissue portions have an areal dimension that is less than about 1 mm$^2$ and/or where at least two of the tissue portions has a dimension that is less than about 1 mm), and where the device provides contraction or expansion of the skin region in one or more directions; and (ii) adjusting the contraction or expansion by exposing the affixed device to one or more external stimuli that result in a change in a physical characteristic of the affixed device. In some embodiments, the areal dimension is less than or equal to about 1.0 mm$^2$ (e.g., less than or equal to about 0.9 mm$^2$, 0.8 mm$^2$, 0.7 mm$^2$, 0.6 mm$^2$, 0.5 mm$^2$, 0.4 mm$^2$, 0.3 mm$^2$, 0.2 mm$^2$, 0.1 mm$^2$, 0.07 mm$^2$, 0.05 mm$^2$, 0.03 mm$^2$, 0.02 mm$^2$, 0.01 mm$^2$, 0.007 mm$^2$, 0.005 mm$^2$, 0.003 mm$^2$, 0.002 mm$^2$, or 0.001 mm$^2$) or between about 0.001 mm$^2$ and 1.0 mm$^2$ (e.g., as described herein).

In some embodiments, the skin region or treated skin region includes a plurality of incised tissue portions and/or excised tissue portions (e.g., a plurality of holes and/or slits). In some embodiments, at least one (e.g., about 2, 3, 4, 5, 6, 7, 8, 9, 10, 15, 20, 25, 30, 35, 40, 45, 50, 75, 100, or more tissue portions, such as between about 2 and 100 tissue portions, as described herein) of the tissue portions has at least one dimension that is less than about 2.0 mm (e.g., less than or equal to about 1.5 mm, 1 mm, 0.75 mm, 0.5 mm, 0.3 mm, 0.2 mm, 0.1 mm, 0.075 mm, 0.05 mm, or 0.025 mm) or between about 0.025 mm and 2.0 mm (e.g., as described herein). In some embodiments, the plurality of incised tissue portions and/or excised tissue portions include one or more elliptical holes in the skin region. In other embodiments, the plurality of incised tissue portions and/or excised tissue portions includes any useful shape (e.g., a cylinder, hole, slit, elongated strip, or other geometries). In further embodiments, the areal fraction of the skin region to be removed is less than about 70% (e.g., less than about 65%, 60%, 55%, 50%, 45%, 40%, 35%, 30%, 25%, 20%, 10%, or 5%) or between about 5% and 80% (e.g., as described herein). In some embodiments, the plurality of tissue portions are incised or excised in any beneficial pattern within the skin region (e.g., as described herein).

In some embodiments, affixing step (i) is performed within about 30 seconds of incising and/or excising the skin region (e.g., within about 20, 15, 10, 5, 3 seconds or less after forming an incision or excision). In other embodiments, the adjusting step (ii) provides selectively closing or opening the incised tissue portions and/or excised tissue portions. In yet other embodiments, adjusting step (ii) includes adjusting the contraction or expansion across the entire device or a portion of the device. In further embodiments, the method results in controlling pleating in the skin region.

In any embodiment described herein, the devices, dressings, apparatuses, and methods are useful for treating one or more diseases, disorders, or conditions to improve skin appearance, to rejuvenate skin, and/or to tighten skin. Exemplary diseases, disorders, or conditions are described herein and include removal of pigment, tattoo removal, veins (e.g., spider veins or reticular veins), and/or vessels in the skin, as well as treatment of acne, allodynia, blemishes, ectopic dermatitis, hyperpigmentation, hyperplasia (e.g., lentigo or keratosis), loss of translucency, loss of elasticity, melasma (e.g., epidermal, dermal, or mixed subtypes), photodamage, rashes (e.g., erythematous, macular, papular, and/or bullous conditions), psoriasis, rhytides (or wrinkles, e.g., crow's feet, age-related rhytides, sun-related rhytides, or heredity-related rhytides), sallow color, scar contracture (e.g., relaxation of scar tissue), scarring (e.g., due to acne, surgery, or other trauma), skin aging, skin contraction (e.g., excessive tension in the skin), skin irritation/sensitivity, skin laxity (e.g., loose or sagging skin or other skin irregularities), striae (or stretch marks), vascular lesions (e.g., angioma, erythema, hemangioma, papule, port wine stain, rosacea, reticular vein, or telangiectasia), or any other unwanted skin irregularities.

Definitions

By "about" is meant +/−10% of any recited value.

By "incised" tissue portion or "incision" is meant a cut, abrasion, or ablation of tissue, including a tissue portion in a skin region, or the act of cutting, abrading, destroying, or ablating tissue, a skin region, or one or more tissue portions. For example, an incision includes any cut, abrasion, or ablation into tissue, which can result in destruction of tissue or a portion thereof and, thereby, produce one or more holes or slits in the skin region. Exemplary methods of forming incised tissue portions or incisions include use of one or more blades, one or more solid needles, fractional laser ablation, fractional radiofrequency ablation, and/or fractional ultrasonic ablation, any useful tool for forming incisions, or any methods and apparatuses described herein.

By "excised" tissue portion or "excision" is meant a removed tissue, including a tissue portion from a skin region, or the act of removing tissue or one or more tissue portions from a skin region. For example, an excision includes any removed tissue or tissue portion from a skin region, which can result in excised tissue portions having a particular geometry (e.g., a cylindrical geometry) and produce one or more holes (i.e., negative space created by the removal of tissue) in the skin region. Exemplary methods of forming excised tissue portions or excisions include use of one or more hollow needles (optionally include one or more notches, extensions, protrusions, and/or barbs), one or more microaugers, one or more microabraders, any useful tool for forming excisions, or any methods and apparatuses described herein.

By "physical characteristic" is meant a physical property of a device (e.g., a dressing) or a material included in the device. Exemplary physical characteristics include compression (or compressive force), expansion, tension (e.g., as measured by tensile stress), structure, size, porosity, surface chemistry, bending modulus, fracture or failure strain, resilience, permeability, swelling ratio, elasticity (e.g., as measured by ultimate modulus of elasticity from the end-portion of stress-strain curves that is greater than 10 N/mm$^2$), electric conductivity, plasticity, resilience, resistance (e.g., as measured by creep resistance), strength (e.g., as measured by Young's modulus (e.g., a Young's modulus that is greater than about 1×10$^5$ N/m), tensile strength (e.g., a tensile strength that is greater than about 2 N/mm$^2$), compressive strength, impact strength, or yield strength), stress (e.g., as measured by compressive stress, shear stress, or tensile stress), load, strain (e.g., as measured by deflection, deformation, strain at failure, or ultimate strain (extension before rupture), e.g., greater than about 30% or from about 30% to 130%), and other parameters, as well as any described herein.

By "pleating" or "skin pleating" is meant any distortion in skin tissue (e.g., in the epidermal and/or dermal layers) that results in puckering and/or folding. An exemplary schematic of skin pleating is provided in FIG. 6.

By "tunable" is meant capable of being adjusted, modified, or altered in one or more physical characteristics in response to one or more external stimuli. Any part of the device can be tunable. For instance, in a dressing, the regulatable layer and/or adhesive layer is tunable. In one non-limiting example, a tunable dressing is a dressing including at least one layer, where the structure of the layer changes in response to an external stimulus, such as a change in temperature. In another non-limiting example, a tunable dressing is a dressing including at least one material, where the structure of the material changes in response to an external stimulus. The change in one physical characteristic (e.g., change in structure at the molecular, microscopic, or macroscopic level) can exert a change in another physical characteristic (e.g., a change in compressive force or tension exerted by the dressing) in one or more directions (e.g., in the x-, y-, z-, xy-, xz-, yz-, and/or xyz-direction). In one non-limiting example, a polymeric material can be optimized to facilitate change in structure at the molecular level by altering the structure of the polymer chain (e.g., alterations to the side chain, linker regions, and/or precursor monomers), the particular block of the polymer (e.g., alterations to length, molecular weight, hydrophobicity, or hydrophilicity), or one or more co-polymeric blocks (e.g., alterations to weight percentage ratios or post-polymerization modifications). The extent of change can be either an increase or a decrease in a physical characteristic, as compared to before exposure of the stimulus. Such an increase or decrease can be of any useful extent, e.g., an increase or decrease of at least about 0.5% (e.g., at least about 0.6%, 0.7%, 0.8%, 0.9%, 1.0%, 1.1%, 1.2%, 1.5%, 1.7%, 2.0%, 2.2%, 2.5%, 2.7%, 3%, 3.5%, 4%, 4.5%, 5%, 5.5%, 6%, 6.5%, 7%, 7.5%, 8%, 8.5%, 9%, 9.5%, 10%, 10.5%, 15%, 20%, 3.5%, 0.5% to 3%, 0.5% to 2.7%, 0.5% to 2.5%, 0.5% to 2.2%, 0.5% to 2.0%, 0.5% to 1.7, 0.5% to 1.5%, 0.5% to 1.2, 0.5% to 1.1%, 0.5% to 1.0%, 0.5% to 0.9%, 0.5% to 0.8%, 0.5% to 0.7%, 0.5% to 0.6%, 0.7% to 20%, 0.7% to 15%, 0.7% to 10.5%, 0.7% to 10%, 0.7% to 9.5%, 0.7% to 9%, 0.7% to 8.5%, 0.7% to 8%, 0.7% to 7.5%, 0.7% to 7%, 0.7% to 6.5%, 0.7% to 6%, 0.7% to 5.5%, 0.7% to 5%, 30%, 35%, 40%, 45%, 50%, 55%, 60%, or more) or from about 0.5% to 20% (e.g., from about 0.5% to 15%, 0.5% to 10.5%, 0.5% to 10%, 0.5% to 9.5%, 0.5% to 9%, 0.5% to 8.5%, 0.5% to 8%, 0.5% to 7.5%, 0.5% to 7%, 0.5% to 6.5%, 0.5% to 6%, 0.5% to 5.5%, 0.5% to 5%, 0.5% to 4.5%, 0.5% to 4%, 0.5% to 0.7% to 4.5%, 0.7% to 4%, 0.7% to 3.5%, 0.7% to 3%, 0.7% to 2.7%, 0.7% to 2.5%, 0.7% to 2.2%, 0.7% to 2.0%, 0.7% to 1.7%, 0.7% to 1.5%, 0.7% to 1.2%, 0.7% to 1.1%, 0.7% to 1.0%, 07% to 0.9%, 0.7% to 0.8%, 1.0% to 20%, 1.0% to 15%, 1.0% to 10.5%, 1.0% to 10%, 1.0% to 9.5%, 1.0% to 9%, 1.0% to 8.5%, 1.0% to 8%, 1.0% to 7.5%, 1.0% to 7%, 1.0% to 6.5%, 1.0% to 6%, 1.0% to 5.5%, 1.0% to 5%, 1.0% to 4.5%, 1.0% to 4%, 1.0% to 3.5%, 1.0% to 3%, 1.0% to 2.7%, 1.0% to 2.5%, 1.0% to 2.2%, 1.0% to 2.0%, 1.0% to 1.7%, 1.0% to 1.5%, 1.0% to 1.2%, 1.0% to 1.1%, 1.5% to 20%, 1.5% to 15%, 1.5% to 10.5%, 1.5% to 10%, 1.5% to 9.5%, 1.5% to 9%, 1.5% to 8.5%, 1.5% to 8%, 1.5% to 7.5%, 1.5% to 7%, 1.5% to 6.5%, 1.5% to 6%, 1.5% to 5.5%, 1.5% to 5%, 1.5% to 4.5%, 1.5% to 4%, 1.5% to 3.5%, 1.5% to 3%, 1.5% to 2.7%, 1.5% to 2.5%, 1.5% to 2.2%, 1.5% to 2.0%, 1.5% to 1.7%, 2.0% to 20%, 2.0% to 15%, 2.0% to 10.5%, 2.0% to 10%, 2.0% to 9.5%, 2.0% to 9%, 2.0% to 8.5%, 2.0% to 8%, 2.0% to 7.5%, 2.0% to 7%, 2.0% to 6.5%, 2.0% to 6%, 2.0% to 5.5%, 2.0% to 5%, 2.0% to 4.5%, 2.0% to 4%, 2.0% to 3.5%, 2.0% to 3%, 2.0% to 2.7%, 2.0% to 2.5%, 2.0% to 2.2%, 2.5% to 20%, 2.5% to 15%, 2.5% to 10.5%, 2.5% to 10%, 2.5% to 9.5%, 2.5% to 9%, 2.5% to 8.5%, 2.5% to 8%, 2.5% to 7.5%, 2.5% to 7%, 2.5% to 6.5%, 2.5% to 6%, 2.5% to 5.5%, 2.5% to 5%, 2.5% to 4.5%, 2.5% to 4%, 2.5% to 3.5%, 2.5% to 3%, 2.5% to 2.7%, 3.0% to 20%, 3.0% to 15%, 3.0% to 10.5%, 3.0% to 10%, 3.0% to 9.5%, 3.0% to 9%, 3.0% to 8.5%, 3.0% to 8%, 3.0% to 7.5%, 3.0% to 7%, 3.0% to 6.5%, 3.0% to 6%, 3.0% to 5.5%, 3.0% to 5%, 3.0% to 4.5%, 3.0% to 4%, 3.0% to 3.5%, 4.0% to 20%, 4.0% to 15%, 3.5% to 10.5%, 4.0% to 10%, 4.0% to 9.5%, 4.0% to 9%, 4.0% to 8.5%, 4.0% to 8%, 4.0% to 7.5%, 4.0% to 7%, 4.0% to 6.5%, 4.0% to 6%, 4.0% to 5.5%, 4.0% to 5%, 4.0% to 4.5%, 5.0% to 20%, 5.0% to 15%, 5.0% to 10.5%, 5.0% to 10%, 5.0% to 9.5%, 5.0% to 9%, 5.0% to 8.5%, 5.0% to 8%, 5.0% to 7.5%, 5.0% to 7%, 5.0% to 6.5%, 5.0% to 6%, or 5.0% to 5.5%), 20% to 30%, 30% to 40%, 30% to 50%, or 50% to 60% as compared to before exposure of a stimulus. For a particular device (e.g., a dressing), further tunability can be accomplished by any processing or post-processing known in the art (e.g., by using one or more hydrophilic or hydrophobic coatings, hydrogels, foams, colloids, etc.), thereby providing further control of one or more physical characteristics.

By "subject" is meant a human or non-human animal (e.g., a mammal).

By "treating" a disease, disorder, or condition in a subject is meant reducing at least one symptom of the disease, disorder, or condition by affixing a device (e.g., a dressing) to the subject.

By "prophylactically treating" a disease, disorder, or condition in a subject is meant reducing the frequency of occurrence or severity of (e.g., preventing) a disease, disorder or condition by affixing a device (e.g., a dressing) to the subject prior to the appearance of a symptom of the disease, disorder, or condition.

Other features and advantages of the invention will be apparent from the following Detailed Description and the claims.

BRIEF DESCRIPTION OF THE DRAWINGS

FIG. 2 shows an exemplary dressing having a regulatable layer and an adhesive layer.

FIGS. 3A-3C describe an exemplary method of tightening skin in a preferred direction. This method includes (FIG. 3A) forming holes in the skin surface and either (FIG. 3B) tightening the skin with non-directional tightening (i.e., directional tightening along both the x- and y-axis) or (FIG. 3C) tightening the skin with directional tightening along the x-axis.

FIGS. 4A-4B show two exemplary dressings that provide non-directional tightening (FIG. 4A) or directional tightening (FIG. 4B).

FIG. 5 shows an exemplary dressing that provides tightening along the x- and y-axis of the dressing, where tightening or contraction can be controlled independently.

DETAILED DESCRIPTION

Figure 1:
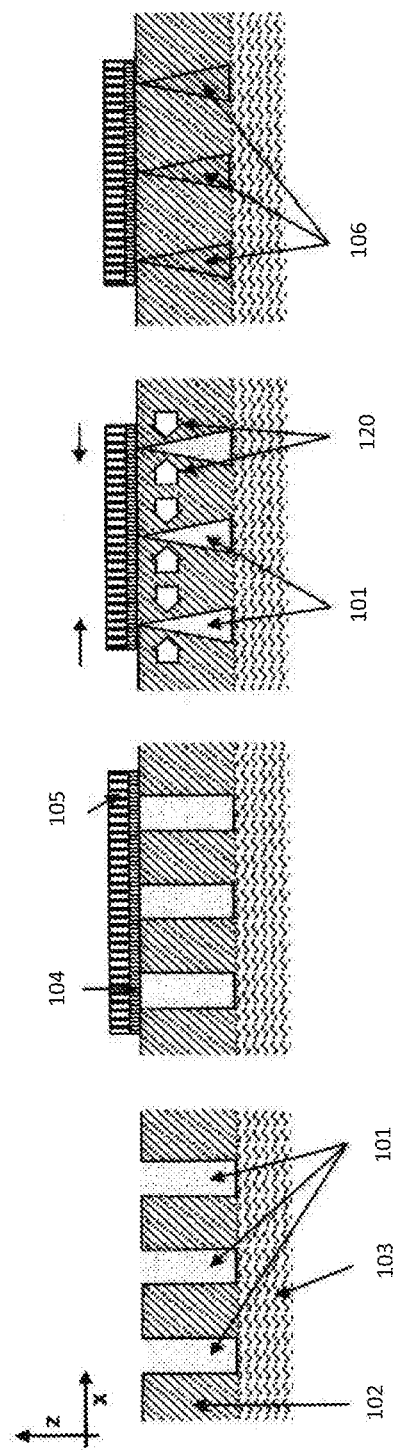
FIGS. 1A-1D describe an exemplary method of tightening skin with a tunable dressing. This method includes (FIG. 1A) forming holes through the dermal and epidermal layer, (FIG. 1B) applying a dressing on the holes in a tensionless state, in which the dressing adheres to the skin surface, (FIG. 1C) activating the tension-regulation layer (or regulatable layer) of the dressing by, e.g., altering the dimension of the dressing (shrinking) and thereby applying a lateral compression force on the small holes, and (FIG. 1D) closing the holes by lateral compression forces, thereby allowing for filling of any remaining space in the holes with new tissue and completing the healing process.

This invention relates to methods and devices for the tightening of skin and/or reduction of skin laxity by selectively opening or closing a plurality of small wounds formed by incision or excision of tissue.

For example, tissue excision can be performed by fractional ablation of the epidermal and/or dermal layer of the skin with a hollow coring needle, by fractional laser ablation, by fractional radiofrequency ablation, and/or by fractional ultrasonic ablation. Various methods and devices are proposed to close the small wounds, including tunable or smart dressings that allow for titration of the tightening effect after application to the skin of a patient.

In particular embodiments, the present invention provides one or more of the following advantages. First, the methods and devices herein enable visualization of results in real time during the course of the treatment. One can envision asking the patient for feedback in real time during the treatment and adjusting the tightening to the patient preference. Second, the methods and devices herein are tunable, thereby allowing for titration of tightening after surgical hole or slit formation. For example, the tunable or smart dressings described herein allow adjustment of the tightening intensity, direction, and spatial distribution after the dressing has been applied or affixed to the patient's skin. In another example, titratable tightening can be achieved by selectively closing or opening a subset of slits or holes produced in an array. Third, the methods and devices herein requires less skill than that of a surgeon. One can envision treatment of patients in an outpatient setting, rather than requiring an inpatient, surgical setting. Fourth, the methods and devices herein constitute minimally invasive techniques, which can provide more predictable results and/or risk factors than that for more invasive techniques (e.g., plastic surgery) or non-invasive energy-based techniques (e.g., laser, radiofrequency, or ultrasound). Fifth, the methods and devices herein can allow for less discriminate methods for treating the skin by forming holes or slits because the methods and devices allow for more discriminate control for closing such holes or slits. Sixth, the methods and devices herein can allow for rapid closing of holes or slits after treating the skin (e.g., within a few seconds after treating skin, such as within ten seconds), thereby minimizing the extent of bleeding and/or clotting within the holes or slits. Finally, the methods and devices herein can be useful for maximizing the tightening effect while minimizing healing time by optimizing tightening (e.g., by controlling the extent of skin pleating, such as by increasing the extent of skin pleating for some applications or skin regions and by decreasing the extent of skin pleating for other applications or skin regions, as described herein).

Devices for Closure of Holes

The present invention features methods and devices to tighten skin having one or more incised or excised tissue portions. In particular, exemplary devices include selectively opening or closing of holes and/or slits using a tunable dressing.

Tunable Dressings

The present invention features a tunable dressing having a regulatable layer formed from any useful material(s) (e.g., any described herein, such as a shape-memory polymer). In particular, exposure of the regulatable layer to one or more external stimuli results in a change in a physical characteristic in the material(s). This change can extend across the entire dressing (e.g., across the entire x-, y-, and/or z-direction of the dressing, including planar and non-planar changes) or in a portion or part of the dressing (e.g., at a localized area of the dressing, which has been locally exposed to a stimulus and thereby results in a change in one or more physical characteristics in the x-, y-, and/or z-direction).

Further, the dressing can provide a variable tightening effect across the entire dressing (e.g., varying degrees of tightening across the entire x-, y-, and/or z-direction of the dressing, including planar and non-planar changes) or in a portion or part of the dressing (e.g., varying degrees of tightening at a localized area of the dressing).

Any useful physical characteristic of the device (e.g., dressing) or material in the device can be changed. Exemplary physical characteristics include compression (or compressive force, e.g., lateral compression), expansion (e.g., lateral expansion), tension (e.g., as measured by tensile stress), structure, size, porosity, surface chemistry, bending modulus, fracture or failure strain, resilience, permeability, swelling ratio, elasticity (e.g., as measured by ultimate modulus of elasticity from the end-portion of stress-strain curves that is greater than 10 N/mm$^2$ (e.g., greater than about 15 N/mm$^2$, 20 N/mm$^2$, 25 N/mm$^2$, 30 N/mm$^2$, 35 N/mm$^2$, or 40 N/mm$^2$) or between about 10 N/mm$^2$ and 200 N/mm$^2$ (e.g., about 10 N/mm$^2$ and 150 N/mm$^2$, 10 N/mm$^2$ and 100 N/mm$^2$, 15 N/mm$^2$ and 200 N/mm$^2$, 15 N/mm$^2$ and 150 N/mm$^2$, 15 N/mm$^2$ and 100 N/mm2, 20 N/mm$^2$ and 200 N/mm$^2$, 20 N/mm$^2$ and 150 N/mm$^2$, or 20 N/mm$^2$ and 100 N/mm$^2$)), electric conductivity, plasticity, resilience, resistance (e.g., as measured by creep resistance), strength (e.g., as measured by Young's modulus, such as a Young's modulus that is greater than about 1×10$^5$ NM$^{-2}$ (e.g., greater than about 2.0×10$^5$ N/m$^2$, 2.5×10$^5$ N/m$^2$, 3.5×10$^5$ N/m$^2$, 4×10$^5$ N/m$^2$, 4.5×10$^5$ N/m$^2$, 5×10$^5$ N/m$^2$, 6×10$^5$ N/m$^2$, 7×10$^5$ N/m$^2$, 8×10$^5$ N/m$^2$, 6×10$^5$ N/m$^2$, or 10×10$^5$ N/m$^2$), tensile strength, such as a tensile strength that is greater than about 2 N/mm$^2$ (e.g., greater than about 5 N/mm$^2$, 7 N/mm$^2$, 10 N/mm$^2$, 15 N/mm$^2$, 17 N/mm$^2$, 20 N/mm$^2$, 25 N/mm$^2$, 27 N/mm$^2$, 30 N/mm$^2$, or 35 N/mm$^2$) or between about 5 N/mm$^2$ and 40 N/mm$^2$ (e.g., between about 15 N/mm$^2$ and 30 N/mm$^2$, 15 N/mm$^2$ and 35 N/mm$^2$, 10 N/mm$^2$ and 30 N/mm$^2$, or 10 N/mm$^2$ and 35 N/mm$^2$), compressive strength, impact strength, or yield strength), stress (e.g., as measured by compressive stress, shear stress, or tensile stress), load (e.g., load per millimeter width of at least 0.1 Newtons at a strain of at least 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or higher), strain (e.g., as measured by deflection, deformation, strain at failure, or ultimate strain (extension before rupture), e.g., greater than about 30% (e.g., greater than about 40%, 50%, 60%, 70%, 75%, 80%, 90%, 95%, 100%, 110%, 115%, or 120%) or from about 30% to 130% (e.g., about 30% to 120%, 30% to 115%, 30% to 110%, 30% to 100%, 30% to 95%, 30% to 90%, 30% to 85%, 30% to 80%, 30% to 75%, 30% to 70%, 30% to 65%, 30% to 60%, 30% to 55%, 30% to 50%, 35% to 130%, 35% to 120%, 35% to 115%, 35% to 110%, 35% to 100%, 35% to 95%, 35% to 90%, 35% to 85%, 35% to 80%, 35% to 75%, 35% to 70%, 35% to 65%, 35% to 60%, 35% to 55%, 35% to 50%, 40% to 130%, 40% to 120%, 40% to 115%, 40% to 110%, 40% to 100%, 40% to 95%, 40% to 90%, 40% to 85%, 40% to 80%, 40% to 75%, 40% to 70%, 40% to 65%, 40% to 60%, 40% to 55%, 40% to 50%, 50% to 130%, 50% to 130%, 50% to 120%, 50% to 115%, 50% to 110%, 50% to 100%, 50% to 95%, 50% to 90%, 50% to 85%, 50% to 80%, 50% to 75%, 50% to 70%, 50% to 65%, 50% to 60%, 50% to 55%, 60% to 130%, 60% to 120%, 60% to 115%, 60% to 110%, 60% to 100%, 60% to 95%, 60% to 90%, 60% to 85%, 60% to 80%, 60% to 75%, 60% to 70%, 60% to 65%, 70% to 130%, 70% to 120%, 70% to 115%, 70% to 110%, 70% to 100%, 70% to 95%, 70% to 90%, 70% to 85%, 70% to 80%, 70% to 75%, 75% to 130%, 75% to 120%, 75% to 115%, 75% to 110%, 75% to 100%, 75% to 95%, 75% to 90%, 75% to 85%, 75% to 80%, 80% to 120%, 80% to 115%, 80% to 110%, 80% to 100%, 80% to 95%, 80% to 90%, or 80% to 85%)), and other parameters.

Further, the extent or intensity of the physical characteristic can be increased or decreased after exposure to one or more stimuli. Exemplary physical characteristics include an increase in tension, a decrease in tension (e.g., of the dressing), an increase in compressive force (e.g., lateral compressive force that is exerted by the dressing), a decrease in compressive force (e.g., lateral compressive force that is exerted by the dressing), compression in one or more directions of the dressing, and/or expansion in one or more directions of the dressing.

The change in one or more physical characteristics can be optimized based on the desired response to a stimulus, location of the skin region to be treated, or any other useful parameter. For instance, the change in physical characteristic can be optimized for placement in the eye region, where the eye region includes Langer lines having particular directions, and the directionality of compression or expansion exerted by the dressing can be perpendicular to such Langer lines to promote skin tightening. Further, optimization that takes into account Langer lines can be utilized on any area of the body. Langer lines correspond to the orientation of native collagen fibers in the dermis. The closing of ablations (including micro-ablations) following Langer line orientation maximizes wound closure efficiency and tightening, and may be applied to any area of the body.

The directionality of the change in the physical characteristics, relative to the device (e.g., dressing) or skin region, can also be optimized. In particular embodiments, the direction of skin tightening is determined by the directionality of the physical characteristic change. For instance, the direction of the tensile force or compressive force can be in the x-, y-, and/or z-direction with respect to the device or skin region (see, e.g., FIGS. 1A-1D for the x-axis, z-axis, and x-z plane for an exemplary device relative to the skin portion; and FIGS. 3A-3C for the x-axis, y-axis, and x-y plane for an exemplary device relative to the skin portion). An exemplary device providing directional tightening (e.g., directional compression and/or expansion) is provided in FIGS. 4 and 5. In particular embodiments, the device (e.g., a dressing having a regulatable layer and/or an unstretched layer) contracts or expands in one or more directions (e.g., in planar and/or non-planar directions) after exposure to a stimulus. Such a device may be used for any method described herein, such as to reduce pleating. In one particular embodiment, the device compresses the skin in one direction (e.g., along the x-axis) as it expands in another direction (e.g., along the y-axis). In this instance, the surface area covered by the dressing may be reduced or not.

The intensity of the change in the physical characteristic(s), as compared to before exposure to one or more stimuli, can also be optimized. Such optimization can include selection of particular materials (e.g., one or more particular shape-memory polymers or alloys) or combinations of such materials to produce the intended effect (e.g., a combination of a rigid polymer with one or more particular shape-memory polymers or alloys), as well as arrangement (e.g., geometric or random arrangement) of such material(s) within a single layer in a device (e.g., within a single regulatable layer) or in separate multiple layers (e.g., in more than one regulatable layers, such as one, two, three, or more layers) in a device to produce the intended directionality and/or intensity of the physical characteristic(s).

The external stimulus to activate or induce the physical characteristic can be any useful stimulus. Exemplary stimulus includes a change in temperature, pH, light, moisture, solvent or chemical exposure, electric field, and/or magnetic field. In particular embodiments, the device includes one or more materials (e.g., in one or more layers) that can be activated by different external stimuli. An exemplary device is provided in FIG. 5, where the regulatable layer includes a first polymer (i.e., responding to stimulus A) and a second polymer (i.e., responding to stimulus B), where stimulus A and stimulus B are different types of stimuli (e.g., temperature and light) or different characteristics of the same stimulus (e.g., two different wavelengths of light). The first and second polymer can be the same polymer that has been modified, shaped, or processed to respond to different stimuli or different polymers having different chemical characteristics.

Furthermore, the change in physical characteristic or exposure of a stimulus can include the entire device or only a portion of the device. For example, the entire dressing can be exposed to an external stimulus to induce a change in compression over the entire skin region to which the dressing is affixed. Although the change in compression can occur over the entire skin region, the extent or intensity of compression can vary along the x-, y-, and/or z-axes or within the xy-, xz-, yz-, and/or xyz-planes of the skin region. In another example, the dressing can be locally exposed to an external stimulus to induce a change in compression over a portion of the device (i.e., thereby resulting in a change in compression over a portion of the skin region). In particular embodiments, the device (e.g., a dressing having a regulatable layer and/or an unstretched layer) contracts or expands in one or more directions (e.g., in planar and non-planar directions) in a portion of the area of the device after exposure to a stimulus. Such a device may be used for any method described herein, such as to reduce pleating.

Tunability of the dressing can provide numerous benefits. For instance, such tunability can allow for real-time control of compressing and/or expanding the dressing after affixation. This level of control can allow for personalized treatment of the patient based on the disease, disorder, or condition to be treated; the optimal cosmetic effect to be achieved; the optimal closure process to be achieved; and/or the timing and extent of the healing process observed for the particular patient. Furthermore, tunability can allow for less discriminate control over how the incisions or excisions in the skin region are made, as well as more discriminate control over selectively closing or opening the incisions or excisions.

The tunable dressing can be affixed to the entire treated skin region or in a portion of the treated skin region. Directional or non-directional tightening can be achieved by producing a geometric arrangement of incisions and/or excisions that are treated similarly. Alternatively, such tightening can be achieved by a non-geometric arrangement of incisions and/or excisions in which only some of the incisions and/or excisions are opened or closed using a tunable dressing.

The tunable dressing can include an adhesive layer (e.g., formed from any adhesive material described herein). The adhesive layer can be continuous (i.e., a continuous layer of one or more adhesive materials attached to the proximal surface of a dressing) or discontinuous (i.e., a non-continuous layer of one or more adhesive materials attached to the proximal surface of a dressing). The adhesive layer can include any useful arrangement of the adhesive material. For instance, the adhesive layer can be tunable and allows for controlled compression or expansion. In some embodiments, an adhesive layer includes a random, non-geometric, or geometric array of an adhesive material for tunability. In particular embodiments, the array allows for directional or non-directional compression and/or expansion as the dressing compresses and/or expands. In particular embodiments, the adhesive layer is discontinuous and includes an array of an adhesive material (e.g., an array of dots, where each dot gets closer together as the dressing compresses and each dot gets further apart as the dressing expands). Exemplary adhesive materials are described herein and include materials that promote collagen cross-linking, such as riboflavin or Rose Bengal, synthetic glues (e.g., cyanoacrylate, polyethylene glycol, or gelatin-resorcinol-formaldehyde), or biologic sealants (e.g., albumin-based or fibrin-based sealants that promote clotting).

The material(s) of the device can include any useful arrangement or form. Exemplary arrangements include a geometric arrangement of one or more materials within a single layer (e.g., a linear array or a grid of one or more materials in a single regulatable layer; or a linear array or a grid of one or more adhesive materials in a single adhesive layer); a geometric arrangement of one or more materials within multiple layers (e.g., in a multilayer dressing having more than one layer, where each layer includes a linear array or a grid of one or more materials and each linear array or grid is optimized for directional compression or expansion); a random, non-uniform arrangement of one or more materials in a single layer or across a plurality of layers; or combinations thereof. In some embodiments, a layer includes a first array of a first material and a second array of a second material, where each array has a geometric arrangement that promotes directional or non-directional compression or expansion. In particular embodiments, the first array is orthogonal to the second array. The materials can also be in any useful form, e.g., a film, a membrane (e.g., as in temperature shrink wrap), or an actuator having more complex geometries. In other embodiments, an adhesive layer includes an array of an adhesive material, where the array has a random, non-geometric, or geometric arrangement that allows for directional or non-directional compression or expansion as the regulatable layer or dressing compresses and/or expands. In particular embodiments, the adhesive layer is discontinuous and includes an array of an adhesive material (e.g., an array of dots of an adhesive material).

The material(s) of the device can optionally include one or more actuators in any useful arrangement or form. Such actuators can be embedded in one or more materials and in one or more layers (e.g., in the regulatable layer and/or the adhesive layer). Furthermore, the actuators can allow for uniform, non-uniform, or variable control (e.g., compression and/or expansion) across the entire device or in a portion of the device. Thus, actuators can be embedded across the entire device, in a portion of the device, in one layer, or in multiple layers. In particular embodiments, the stimulus-responsive material includes one or more actuators that respond to one or more stimuli, where the material includes a plurality of one type of actuator or a plurality of different actuators. The actuators in each layer can be arranged in any useful random, non-geometric, or geometric arrangement. Alternatively, the actuators can be arranged within multiple layers (e.g., in a multilayer dressing having more than one layer, where each layer includes a linear array or a grid of one or more actuators and each linear array or grid is optimized for directional compression or expansion); a random, non-uniform arrangement of one or more actuators in a single layer or across a plurality of layers; or combinations thereof. Exemplary materials including one or more actuators are described herein.

The material(s) or layer(s) in a device (e.g., a dressing) can include an unstretched layer (e.g., including any material described herein) and an adhesive layer. The unstretched layer can include one or more unstretched materials, including those having sufficient rigidity to hinder stretching and those having one or more stretchable polymers that are not stretched prior to affixing to a skin region. The material(s) or layer(s) in a device (e.g., a dressing) can include an adhesive layer, a regulatable layer, as well as one or more additional, optional layers or fasteners (e.g., staples, sutures, etc.). Exemplary optional layers include an occlusion layer (e.g., to control humidity and/or promote wound healing), an absorption layer (e.g., to absorb wound exudate), a reinforcement layer (e.g., to reinforce the layer and optionally formed from low-density polyethylene (LDPE), fluorinated ethylene propylene (FEP), or nylon), and/or a delivery layer (e.g., to delivery one or more therapeutic agents, as described herein).

The device (e.g., dressing) can optionally include an applicator, as described herein. In some embodiments, the applicator is a frame or any other useful structure that provides sufficient support to the tunable dressing and/or provides a sterile method to affix the tunable dressing to the treated skin region. In other embodiments, the applicator is configured to attach to an apparatus that forms one or more incisions and/or excisions, where the applicator allows for releasing and/or affixing the tunable dressing after the formation of such an incision or excision (e.g., within about 30, 25, 20, 15, 10, 5, 3 seconds or less after forming an incision or excision).

The device can be of any cosmetically appealing color, shape, and/or material. For example, the tunable dressing can be provided in a skin tone color or is transparent or semi-transparent. Such transparent or semi-transparent dressings can additionally be helpful for visualization, e.g., for real-time tunability of the dressing and/or for affixing the dressing to the treated skin region.

Exemplary tunable dressings and materials for constructing such dressing are described herein.

Testing of Devices

To optimized function of any of the devices described herein, the appropriate force (e.g., compressive, tensile, and/or lateral force) and/or geometric arrangement of the device (e.g., a dressing) can be tested by any useful metric. Exemplary metrics include any useful endpoint, such as presence or absence of melanocytes, melanin in keratinocytes, collagen production, elastin, scarring and/or infection, fibroblast activity, inflammation, macrophage and/or leukocyte recruitment, or the relative thickness of the papillary dermis and/or epidermis; melanin index, which is a unitless variable that quantifies the concentration of melanin in skin (e.g., by obtaining a reflectance spectrum and determining the slope of the log of the inverse reflectance values for wavelengths between 620 and 700 nm); erythema index, which is a unitless variable that quantifies the concentration of melanin and/or hemoglobin in skin (e.g., by obtaining an absorption spectrum and determining the log of the ratio of the reflectance at 635 nm and at 565 nm, such as by using a commercially available reflectance instrument from Diastron (Hampshire, U.K.)); transepidermal water loss, which measures the quantity of water that passes from the inside of a body through the epidermal layer; the Glogau wrinkle assessment scale with a scoring system of type I (no wrinkles), type II (wrinkles in motion), type III (wrinkles at rest), and type IV (only wrinkles), as described in Glogau, "Aesthetic and anatomic analysis of the aging skin," *Semin. Cutan. Med. Surg.* 15(3):134-138 (1996); and/or the Fitzpatrick wrinkle assessment scale (FWAS) or modified FWAS (MWAS) with a scoring system of 0 (no wrinkle: no visible wrinkle, continuous skin line), 0.5 (very shallow yet visible wrinkle), 1 (fine wrinkle: visible wrinkle and slight indentation), 1.5 (visible wrinkle and clear indentation with less than 1 mm wrinkle depth), 2 (moderate wrinkle: clearly visible wrinkle with 1 mm to 2 mm wrinkle depth), 2.5 (prominent visible wrinkle with more than 2 mm and up to 3 mm wrinkle depth), and 3 (deep wrinkle: deep and furrow wrinkle with more than 3 mm wrinkle depth).

Further Processing of Devices

The devices (e.g., dressings) can be further processed prior to affixing to the subject. Exemplary processes include sterilization (e.g., with ultrasound, ultraviolet light, heat, and/or plasma); treatment with one or more antimicrobials (e.g., treatment with chlorhexidine gluconate or silver, such as a silver nitrate or $Ag^+$ in one or more useful carriers, as described herein); and/or treatment with one or more agents, e.g., to form a coating on the dressing, where exemplary agents include a biocompatible matrix (e.g., those including at least one of collagen (e.g., a collagen sponge), low melting agarose (LMA), polylactic acid (PLA), and/or hyaluronic acid (e.g., hyaluranon)), a photosensitizer (e.g., Rose Bengal, riboflavin-5-phosphate (R—5-P), methylene blue (MB), N-hydroxypyridine-2-(1H)-thione (N-HTP), a porphyrin, or a chlorin, as well as precursors thereof), a photochemical agent (e.g., 1,8 naphthalimide), a fibrin sealant, a cyanoacrylate adhesive, or a tissue glue composed of a mixture of riboflavin-5-phosphate and fibrinogen Methods of Skin Tightening The present invention relates to various methods and devices (e.g., dressings) used to selectively open or close incisions and/or excisions (e.g., all or a portion of such incisions, such as microslits, and/or excisions, such as holes) formed in the skin region by the incised or excised tissue portions. The devices can be affixed to the entire treated skin region or in a portion of the treated skin region, which allow for directional or non-directional tightening by producing a geometric or non-geometric arrangement of incisions and/or excisions that are treated similarly or differently. Further, the devices can provide uniform or non-uniform compression and/or expression across the entire device or a portion thereof. Accordingly, these methods and devices can result in reducing the skin surface and/or tightening of the skin.

The methods can include contraction or expansion in one or more directions in at least a portion of the device (e.g., the dressing). The methods include, for example, affixing a device to a skin region having a plurality of incised tissue portions and/or excised tissue portions (e.g., where at least two of said tissue portions has at least one dimension that is less than about 1 mm or an areal dimension that is less than about 1 $mm^2$). The device provides contraction or expansion of the skin region in one or more directions (e.g., in the x-, y-, z-, xy-, xz-, yz-, and/or xyz-directions, as described herein), where such contraction or expansion can be uniform or non-uniform. Furthermore, contraction or expansion arises by exposing an affixed device to one or more external stimuli (e.g., any described herein) that results in a change in a physical characteristic of the device. In addition, such contraction and/or expansion can be adjusted after affixing the device. For example, after treating the skin and affixing the device, the device can result in expansion of the skin region and then later exposed to an external stimulus to further expand or to compress the skin region. In this manner, the device is tunable.

The present invention also includes methods of tightening skin in a preferred direction. An exemplary method is provided in FIGS. 3A-3C, which show (in FIG. 3A) the skin surface (top view, x-y plane) before closure of the small holes and (in FIG. 3B) after non-directional tightening or (in FIG. 3C) after directional tightening along the x-axis. This method is described in detail herein. Directional tightening of the skin (e.g., by compression and/or expansion exerted by the device) can be optimized by using one or more materials in one or more layers of the device. Such compression and/or expansion can be controlled independently (e.g., by use of one or more stimuli).

The present invention also includes optimizing the dimension of the incised or excised tissue portions to promote wound healing. Exemplary dimensions include circular and non-circular holes, such as elliptical holes (e.g., as viewed from the xy-plane). Non-circular holes can be formed by using an apparatus having a non-circular cross-section (e.g., a blade or a tube, such as a hollow tube, having a non-circular cross-section) or by pre-stretching the skin before treatment with an apparatus having a circular cross-section (e.g., a circular coring needle generates an elliptical hole in a non-stretched skin). In some embodiments, the long axis of the ellipse is perpendicular to the pre-stretching direction, where the elliptical hole can generate skin tightening preferentially in the direction of the short axis of the ellipse. Accordingly, the devices of the invention (e.g., a dressing, as described herein) can be affixed to a skin portion including one or more elliptical holes or one or more incised or excised tissue portions having one or more elliptical geometries.

The methods and devices herein can allow for less discriminate methods for treating the skin by forming holes or slits because the methods and devices allow for more discriminate control for closing or opening such holes or slits. For instance, tunable dressings allow for real-time control for compressing or expanding holes or slits. Exemplary modes of control include the extent of compression or expansion, the directionality of compression or expansion (e.g., in the x-, y-, z-, xy-, yz-, xz-, or xyz-direction), and/or timing of applying the compression or expansion (e.g., within a few seconds, such as within 30, 20, 15, 10, 5, 3 seconds, or less).

Control of Skin Pleating

Furthermore, the methods and devices of the invention can be used to control skin pleating. For example, when using dressing to compress the skin and close holes and/or slits, it may be advantageous to apply an optimal compression level that can be adjusted during the treatment period and after affixing the dressing. During the setting of the tissue, skin pleating can be beneficial in some instances and should be avoided in other instances. After the excision or incision, the tissue can be compressed or expanded in order to set the tissue. In particular examples, the setting time may be as short as 2-4 days, and the tunable dressing provides compression or expansion prior to this setting time. Accordingly, the methods and devices or the invention can be used to control the level of compression and/or expansion exerted by the device to increase and/or decrease the extent of skin pleating.

Figure 6:
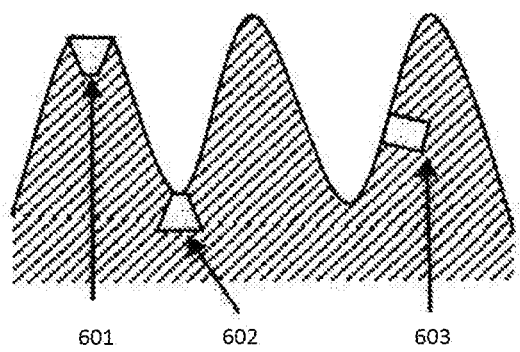
FIG. 6 describes the potential effect of pleating on the geometry of holes formed in skin.

The state of the tissue can provide feedback about the optimal compression level, such that tissue pleating can be controlled. Tissue pleating may affect the wound healing process, where FIG. 6 shows an exemplary effect of pleating on hole geometry. Furthermore, in some instances, pleating may prevent conformal adhesion of the device with the treated skin region, thereby affecting the function of a wound dressing that requires contact with the skin. Accordingly, pleating can be controlled by inspecting the skin periodically and adjusting the tunable dressing affixed to the skin region (e.g., by exposure of one or more external stimuli). Alternatively, the dressing can control pleating by having limited flexibility (e.g., by including one or more rigid materials or unstretched materials, as described herein) or limited flexibility in particular areas and/or directions. In one particular example, pleating can be controlled by minimizing the size of the compressed area. For example, the methods include the use of a tunable dressing having multiple, smaller compression areas proximal to each other, separated and/or surrounded by non-compressed areas. Tunable dressings that exploit this compression area format are also included in the invention.

The methods and devices for skin tightening can also be optimized for conforming to uneven skin surfaces, whether such surfaces arise from a particular disease or condition (e.g., any described herein) or from the anatomical location of the skin region (e.g., in the brow, chin, or breast regions). Such unevenness can occur in any direction or plane, including non-planar and planar unevenness. In some embodiments, the tunable dressing includes one or more materials that allow for contraction or expansion of the skin region in one or more directions (e.g., in the x-, y-, z-, xy-, xz-, yz-, and/or xyz-directions, as described herein), as well as in planar and non-planar directions (e.g., in the xy-, xz-, yz-, and/or xyz-planes). When treating uneven skin surfaces, tissue pleating can be a particular concern that should be controlled. Thus, the methods, devices, and tunable dressing described herein can be useful for optimizing compression and/or expansion levels in any useful direction(s) for treating uneven skin surfaces, while controlling pleating.

Materials

The methods, devices, and apparatuses of the invention can include any useful materials. In a tunable dressing, the regulatable layer can include one or more stimulus-responsive materials (e.g., a shape-memory material, a shape-memory polymer, a shape-memory alloy, a thermal-responsive material, a pH-responsive material, a light-responsive material, a moisture-responsive material, a solvent-responsive or chemical exposure-responsive material, an electric field-responsive material, a magnetic field-responsive material, an actuator-embedded material, and/or an unstretched material). The adhesive layer can include one or more adhesive materials (e.g., pressure sensitive adhesives).

The materials can include arise from any useful mechanism for compressing and/or expanding the device, as well as any useful stimulus. Such mechanisms include mechanical, hydraulic, and/or pneumatic modes of operation. Exemplary stimulus includes a change in temperature, pH, light, moisture, solvent, chemical exposure, electric field, and/or magnetic field, which can optionally result in mechanical, hydraulic, and/or pneumatic tuning.

The materials can be of any useful form. Exemplary forms include an emulsion, a fiber, a film, a foam, a hydrogel, a solution, a laminate, or any other form that can be further processed, such as shaped, cast, extruded, molded (e.g., by blow molding, injection molding, or resin transfer molding), woven, cross-linked, deposited, laminated, and/or spun (e.g., by wet spinning, electrospinning, and/or melt spinning) to any useful article (e.g., a dressing or one or more layers within a dressing).

Shape-Memory Materials

Shape-memory materials (SMMs) can change their physical conformation (or shape) under an external stimulus (e.g., a thermal stimulus). For example, an article formed from an SMM or coated with an SMM can possess a first, desired shape and a second, temporary shape. When the SMM is regulatable by temperature, switching between these two shapes is achieved by heating or cooling above the glass or melting transition temperature of the SMM. SMMs may have a completely reversible transition (e.g., in a material that returns to its original shape) or a partially reversible transition with hysteresis (e.g., resulting in a material requiring additional energy to return to its original shape). SMMs can have multiple external stimulus responses, such as responses to both temperature and light or temperature and magnetic fields.

SMMs include both shape-memory polymers (SMPs) and shape-memory alloys (SMAs). SMPs can be in any useful form, such as in the form of the parent polymer chain, gels, hydrogels, emulsions, or micelles. Exemplary SMPs include shape-memory polyurethane (e.g., a poly(propylene glycol) (PPG), 4,4'-diphenylmethane diisocyanate (MDI), and dimethylolpropionic acid (DMPA) (PPG/MDI/DMPA) copolymer, where —NCO is optionally end-capped with methyl ethyl ketoxime (MEKO), or polymers including dimethyloldihydroxyethylene urea (DMDHEU) and/or 1,2,3,4-butane tetra-carboxylic acid (BTCA)); a poly(ethylene terephthalate)/poly(caprolactone) (PET/PCL) block copolymer (e.g., optionally crosslinked with maleic anhydride, glycerin, or dim ethyl 5-isophthalate); a polyethylene terephthalate/polyethylene oxide (PET/PEO) block copolymer; an ABA triblock copolymer made from poly(2-methyl-2-oxazoline) and polytetrahydrofuran; a polystyrene and poly(1,4-butadiene) (PS/PBD) block copolymer; a polyethylene glycol/4,4'-diphenylmethane diisocyanate/pentaerythritol (PEG/MDI/PE) copolymer; polynorbornene (($C_7H_{10}$)$_x$ or Norsorex®, available from Astrotech Advanced Elastomer Products GmbH, Vienna, Austria); organic-inorganic hybrid polymers including polynorbornene units partially substituted by polyhedral oligosilsesquioxane (FOSS); an acrylate-based polymer; a styrene-based polymer; an epoxy-based polymer); and shape-memory fibers (e.g., oligomers prepared with polyol as the soft segment and small size diols and MDI as the hard segment).

Exemplary SMAs include a nickel-titanium (NiTi) alloy (e.g., Nitinol™, available from Nitinol Devices & Components, Inc., Fremont, Calif., of approximately 55% Ni); a nickel-titanium-niobium (NiTiNb) alloy; a nickel-iron-gallium (NiFeGa) alloy; a nickel-manganese-gallium (NiMnGa) alloy; a copper-aluminum-nickel (CuAlNi) alloy (e.g., 14/14.5 wt. % Al and 3/4.5 wt. % Ni); a copper-zinc (CuZn) alloy (e.g., 38.5/41.5 wt. % Zn); a copper-tin (CuSn) alloy (e.g., approximately 15 at. % Sn); a copper-zinc-aluminum (CuZnAl) alloy; a copper-zinc-silicon (CuZnSi) alloy; a copper-zinc-tin (CuZnSn) alloy; a copper-manganese alloy (e.g., 5/35 at. % Cu); a gold-cadmium (AuCd) alloy (e.g., 46.5/50 at. % Cd); a silver-cadmium (AgCd) alloy (e.g., 44/49 at. % Cd); an iron-platinum (FePt) alloy (e.g., approximately 25 at. % Pt); an iron-manganese-silicon (FeMnSi) alloy (e.g., approximately 25 at. % Pt); a cobalt-nickel-aluminum (CoNiAl) alloy; a cobalt-nickel-gallium (CoNiGa) alloy; or a titanium-palladium (TiPd) alloy.

SMMs can also include shape-memory composites (SMC) and shape-memory hybrids (SHC). SMCs and SMHs are dual component systems that include at least one SMM integrated with conventional materials. Exemplary conventional materials include those useful for preparing wound care dressings, such as any described herein and include, e.g., alginate, benzyl hyaluronate, carboxymethylcellulose, cellulose acetate, chitosan, collagen, dextran, epoxy, gelatin, hyaluronic acid, hydrocolloids, nylon (e.g., nylon 6 or PA6), pectin, poly (3-hydroxyl butyrate-co-poly (3-hydroxyl valerate), polyacrylate (PA), polyacrylonitrile (PAN), polybenzimidazole (PI31), polycarbonate (PC), polycaprolactone (PCL), polyester (PE), polyethylene glycol (PEG), polyethylene oxide (PEO), PEO/polycarbonate/polyurethane (PEO/PC/PU), poly(ethylene-co-vinyl acetate) (PEVA), PEVA/polylactic acid (PEVA/PLA), poly (ethylene terephthalate) (PET), PET/poly (ethylene naphthalate) (PET/PEN) polyglactin, polyglycolic acid (PGA), polyglycolic acid/polylactic acid (PGA/PLA), polyimide (PI), polylactic acid (PLA), poly-L-lactide (PLLA), PLLA/PC/polyvinylcarbazole (PLLA/PC/PVCB), poly ((3-malic acid)-copolymers (PMLA), polymethacrylate (PMA), poly (methyl methacrylate) (PMMA), polystyrene (PS), polyurethane (PU), poly (vinyl alcohol) (PVA), polyvinylcarbazole (PVCB), polyvinyl chloride (PVC), polyvinylidenedifluoride (PVDF), polyvinylpyrrolidone (PVP), silicone, rayon, or combinations thereof.

Exemplary SMCs include dual component systems including SMM materials in contact with conventional materials, such that the conventional material applies a force to bend the SMM absent an external stimulus. Upon the addition of an external stimulus, the SMM changes shape, thus overcoming the force applied from the conventional material. The resulting shape transition moves both the SMM and conventional components. In addition, SMHs exhibit the characteristic shape transitions of SMM but are constructed from conventional materials (e.g., non-shape-memory materials). Exemplary SMHs include dual region plastic materials constructed of two conventional polymers layers, where the material bends in response to temperature changes due to the difference in thermal expansion between the two plastic layers. Additional exemplary SMC and SHC materials can be found in, e.g., in Huang et al., "Shape memory materials," *Materials Today* 13:54-64 (2010), which is hereby incorporated by reference in its entirety.

Thermal-Responsive Materials

Thermal-responsive materials can change their physical and chemical properties upon changes in temperature. The transition temperature is the temperature at which the polymer's characteristics change and includes a lower critical solution temperature (LOST) or an upper critical solution temperature (UCST). A common, exemplary response to temperature change is a transition in the hydrophilic/hydrophobic character of the material. A transition to a more hydrophobic state results from changes in the polymer's ability to hydrogen bond with the surrounding environment (e.g., a solvent or solution). For a thermal-responsive polymer dissolved in solution, the temperature response can result in a transition in the polymer's conformation and solvent interaction. This transition includes an expanded state with extensive solvent interaction and a contracted state with limited solvent interaction. In the contracted state, the thermal-responsive polymer will become insoluble and precipitate from solution.

The same above-described transition can occur in other forms (e.g., in gels, such as in hydrogels in which the cross-linked polymer is swollen by a solvent, or in copolymers). Upon exposure to a temperature transition, the conformation of the polymer network changes, thus resulting in reduced solvent interactions and causing a reduction in the gel's volume. Often the transition temperature is independent of the polymer's molecular weight. The transition temperature can be modified with changes to the solvent system. For example, the addition of cosolvents or salts can increase or decrease the transition temperature. For copolymers, the transition temperature in aqueous environments is generally decreased with the addition of more hydrophobic co-monomers or polymer modifying groups. Alternatively, the transition temperature is generally increased by the addition of more hydrophilic co-monomers or polymer modifying groups.

Exemplary thermal-responsive materials include poly-N-isopropylacrylamide (poly-NIPAAm, LCST at 32-37° C.); poly-N-vinylcaprolactam (LCST at 25-35° C.); poly-N,N-diethylacrylamide (LCST at 25¬32° C.); other polyalkylacrylamides and co-polymers of polyalkylacrylamides; polyethylene glycol; polyethylene oxide (PEO, LCST at about 85° C.); polypropylene oxide (FPO); polymethylvinyl ether (LCST at 34-38° C.); and PEO-PPO copolymers. Exemplary thermal-responsive gels or hydrogels include copolymer networks of include poly-N-isopropylacrylamide, poly-N-vinylcaprolactam, poly-N,N-diethylacrylamide, and other polyalkylacrylamides with a cross-linker, such as methylene bisacrylamide. Such thermal-responsive materials can be provided in any form, such as heat shrink films.

pH-Responsive Materials pH-responsive materials can change their physical and chemical properties upon changes in pH. A transition can arise from increased charge density resulting from protonation or deprotonation of a polymer or from decreased charge density resulting from neutralization of the polymer. In general, increasing the charge density results in increased hydrophilicity, which in turn promotes interactions with water, polar solvents, or salts. Decreasing charge density typically makes the polymer more hydrophobic and reduces the interactions with water, polar solvents, and salts.

The nature of the pH transition results from the type of acid/base functionalities present in the material. For example, the presence of amine functionalities (e.g., moieties with a high pKa) results in higher charge densities as the pH decreases and neutralization of the charge as the pH increases. Conversely, the presence of carboxylic acid functionalities (e.g. moieties with a low pKa) results in higher charge densities as the pH increases and neutralization of the charge as the pH decreases. For a pH-responsive polymer in solution, a transition from a higher charge density to a lower charge density (e.g., neutralization of charge) can result in the polymer becoming insoluble and precipitating from solution. An insoluble pH-responsive polymer can dissolve into water as the charge density is increased (e.g. increasing pH for a carboxylic acid moiety containing polymer). The same pH-response transition can occur in numerous forms, such as gels or hydrogels. Typically, an increasing charge density causes the gel network to swell with water, polar solvents, or salts, thus expanding the gel's volume. Conversely, the neutralization of charge results in a reduction of the gel volume due to the elimination of water, polar solvents or salts from the network.

Exemplary pH-responsive polymers include polyacrylic acid, polymethacrylic acid, and methacrylic acid/methyl methacrylate copolymers (Eudragit®, Evonik Industries AG); copolymers of polyacrylic acid and polyvinyl alcohol (PAA/PVA); carboxylic acid derivatives of styrene; derivatives of cellulose such as carboxymethylethylcellulose, cellulose acetate-phthalate and diethylaminoethyl cellulose; diethylaminoethyl methacrylate/methyl methacrylate or butyl methacrylate copolymers (e.g., insoluble at pH 7, soluble at acidic pH); polypyridine; polyallylamine, polyvinylamine, chitosan, and other polyamines; as well as N-dimethylaminoethyl methacrylate, biodegradable copolymers of N,N-dimethylacrylamide, N-tert-butyl acrylamide and N-methylacryoylglycylglycine p-nitrophenyl ester. Exemplary pH-responsive gels or hydrogels include methacrylic acid/methyl methacrylate polymer networks crosslinked with a bifunctional methacrylate, such as 1,4-butanediol dimethacrylate, carboxylic acid derivatives of styrene cross-linked with divinylbenzene; cellulose derivatives cross-linked with multifunctional cross-linking agents such as butanediol diglycidylether; as well as copolymers of polyacrylic acid and polyvinyl alcohol cross-linked with a divinyl group such as 1,4-butanediol dimethacrylate. Exemplary pH-sensitive materials are found, e.g., in Galaev et al., *Russian Chem. Reviews* 64: 471-489 (1995), which is hereby incorporated by reference in its entirety.

Light-Responsive Materials

Light-responsive materials can change their physical and chemical properties upon exposure to electromagnetic radiation. Typically, moieties within the polymer structure undergo a change in response to light of a particular energy. The light provides energy for the moiety to overcome activation energy barriers and transition into a different conformation or state. For example, a copolymer incorporating an azobenzene chromophore has a lower dipole moment (e.g., is less polar) in the trans conformation around the azo double bond. The azobenzene moiety provides a light sensitive "switch," which provides the response to external stimulus. Upon irradiation with light, the double bond can isomerizes to the cis conformation, thus increasing the dipole moment (e.g., making the polymer more polar). The increase in polarity can result in increased solubility in polar solvents. This phenomenon is observed with a dimethylacrylamide-4-phenylazophenylacrylate (7.5 mol %) copolymer. At a temperature slightly above the LOST, the solution is generally cloudy. However, upon UV irradiation, the copolymer's LCST is reduced below the environmental temperature and the solution becomes clear as the copolymer dissolves. Exemplary light-sensitive polymers are found, e.g., in Galaev et al., *Russian Chem. Reviews* 64:471-489 (1995), which is hereby incorporated by reference in its entirety.

Light-responsive polymers include those having one or more of the following light-responsive switches: cinnamic acid, cinnamylidene acetic acid, azobenzene chromophores (e.g., 4-phenylazobenzene), triarylmethylcyanide, stilbene, or quinone-methide moieties.

Moisture-Responsive Materials

Moisture-responsive materials can change their physical and chemical properties upon a change in the environmental humidity or water content. This transition generally involves an increasing or decreasing association with other components in the medium following exposure to water. Essentially, water displaces or increases the volume of the existing medium thus causing changes commiserate with the polymer's hydrophilicity. For example, the grafted polymer, polymethacrylic acid-graft-polyethylene glycol, is collapsed in solutions with a high ethanol/water ratio. Upon addition of water the polymer swells thus increasing the polymers porosity. This volumetric change enables the release of therapeutic compounds after contacting the polymer containing therapeutic compounds with a mucus membrane. This exemplary moisture-sensitive polymer is found in de las Heras Alarcon et al., *Chem. Soc. Rev.* 34:276-285 (2005), which is hereby incorporated by reference in its entirety.

Exemplary moisture-sensitive polymers include copolymers of ionic monomers, such asacrylamidopropane sulfonic acid sodium salt with neutral monomers, such as acrylamide; pH sensitive polymers, as described above with high charge density; and grafted polymers, such as polymethacrylic acid-graft-polyethylene glycol.

Solvent-Responsive or Chemical Exposure-Responsive Materials

Solvent-responsive materials can change their physical and chemical properties upon a change in the solvent or chemical content of the surrounding medium or environment. Similar to the moisture-responsive materials described above, solvent or chemical exposure-responsive materials possess a transition involving an increasing or decreasing association with other components in the medium following exposure to a solvent or chemical. Generally, the solvent responds to displaces or increases the volume of the existing medium, thus causing changes consistent with the polymer's relative compatibility between the exposed solvent and the existing medium. The solvent-responsive material can be a polymer composite with another material or a modified non-polymeric material.

En exemplary chemical-responsive material is a combination of activated carbon and polyaniline were formed into a composite structure or chemiresistive detector. Adsorption of biogenic amines causes a response in the polymer component, which changes the resistance of the composite and yields an electrical signal indicating the presence of the analyte. This exemplary solvent-sensitive polymer composite is found in patent number EP1278061B1, which is hereby incorporated by reference in its entirety Exemplary solvent or chemical exposure-responsive materials include a polymer/carbon blackcomposite, polyaniline/carbon black composite, gold/para-substituted thiophenol, gold clusters encapsulated with octanethiol, and a dendrimer of poly(amidoamine).

Electric Field-Responsive Materials

Electric field-responsive materials can change their physical and chemical properties upon changes to the applied electric field. The electric field-responsive materials can be metal or a composite material including a polymer and metal. In general, the electric field stimulates a electric field sensitive component or electric "switch." The polymer component of electric field-sensitive composites can be made from any polymer with the desired polymer properties.

Electric field-responsive materials include those having one or more of the following switches: carbon black, carbon nanotube, metallic Ni powder, short carbon fibers (SCFs), or super-paramagnetic nanoparticles (e.g., magnetite nanoparticles). Electric field-responsive materials can optionally include any composite or material described herein.

Magnetic Field-Responsive Materials

Magnetic field-responsive materials can change their physical properties upon changes to the applied magnetic field. The magnetic field-responsive materials can be metal or metal polymer composite materials. In general, the magnetic field stimulates a magnetic field sensitive component or magnetic "switch." The polymer component of magnetic field-sensitive composites can be made from any polymer with the desired polymer properties.

Exemplary magnetic field-responsive materials or magnetic switches include magnetite, poly[aniline-co-N-(1-butyric acid)]aniline/iron oxide, polylactide/nanocrystalline magnetite, maghemite, cobalt ferrite, carbonyl iron, ferromagnetic shape-memory alloy, magnetic nanoparticles (e.g., such as iron, cobalt, or iron oxide (e.g., $Fe_3O_4$)), spinel ferrimagnets (e.g., such as $CoFe_2O_4$ and $MnFe_2O_4$), and alloys (e.g., $CoPt_3$ and FePt). Exemplary polymers for magnetic field-responsive composites include any polymer described herein, e.g., high molecular weight polyacrylic acid, polyethylene glycol, poly(2-vinyl-N-methylpyridinium iodide), polystyrene, polyethyleneimine, and block copolymers of polystyrene, such as poly(styrene-b-butadiene-b-styrene). Exemplary magnetic field-sensitive polymers are found, e.g., in Dai et al., *Chem. Soc. Rev.* 39:4057-4066 (2010), which is hereby incorporated by reference in its entirety.

Actuator-Embedded Materials

Actuator-embedded materials can include one or more micro electro-mechanical systems actuators (or MEMS actuators) to change their physical properties upon exposure to one or more stimuli. Such actuator-embedded materials can result in mechanical, hydraulic, and/or pneumatic control of compression and/or expansion of the device. In some embodiments, the actuator-embedded materials include one or more actuators in combination with one or more polymers (e.g., any described herein, including polyvinylidenedifluoride, polyimide, polyester, rayon, epoxy, or combinations thereof). Exemplary actuators includes those made from one or more carbon nanotubes (e.g., single-walled carbon nanotube composites having a piezoelectric effect); one or more piezoceramic actuators (e.g., including lead magnesium niobate (PMN), and optionally having one or more interdigitated electrodes, or one or more $Pb(Zr_xTi_1)O_3(PZT)$ materials (e.g., Ceramic B, PZT-2, PZT-4, PZT-5H, PZT-5A, PZT-4S, or PZT-8M, available from MTC Electro Ceramics, Berkshire, England)); one or more multilayered actuators (e.g., a PZT-based actuator, such as RAINBOW (Reduced And Internally Biased Oxide Wafer); a thin-layered piezoelectric composite material, such as THUNDER (Thin Layer Composite Unimorph ferroelectric DrivER and sensor); a laminate material including piezofibers, interdigitated electrodes, and a polymer (e.g., PVDF or polyimide, such as a Kapton® film), such as an AFC (Active Fiber Composite) developed by MIT University, USA; a macro-fiber composite including uniaxially aligned piezofibers in a polymer matrix, such as LaRC-MFC™ (NASA-Langley Research Center Macro-Fiber Composite); or a composite actuator including a carbon fiber composite layer with near-zero coefficient of thermal expansion (CTE), a PZT ceramic wafer, and a glass/epoxy layer, such as LIPCA (Lightweight Piezo-Composite Actuator)); one or more optical fibers (e.g., quartz-type and single-mode optical fibers, optionally embedded in an epoxy matrix); one or more piezopolymeric films; one or more piezoplates (e.g., a lead zirconate titanate plate that is optionally nickel-plated, e.g., PSI-5A4E or PSI-5H4E, available from Piezo Systems, Inc., Woburn, Mass.); one or more piezofibers (e.g., one or more carbon fibers and/or glass fibers, as well as composites thereof); one or more shape-memory polymers (e.g., any described herein); or one or more shape-memory alloys (e.g., any described herein, such as a NiTi alloy).

Exemplary actuator-embedded materials include carbon nanotubes in combination with polyvinylidenedifluoride (PVDF, optionally as a melt-blended or electrospun composite); carbon nanotubes in combination with polyimide (PI, optionally as a melt-blended or electrospun composite); unidirectional carbon fiber pre-impregnated sheets, such as XN-50A-RS3C, available from TenCate Corp., Nijverdal, Netherlands; Terfenol-D®, a magnetorestrictive material having terbium, iron, and dysprosium (available from Etrema Products Inc., Ames, Iowa); a thermally actuated composite incombination with a microelectronic substrate, such as those described in U.S. Pat. No. 6,211,598, which is hereby incorporated by reference in its entirety; a composite material including a nickel-tin shape-memory alloy (e.g., Nitinol™) in a thin film; or a magnetorestrictive composite including layers of Tb—Fe, polyimide, and Sm—Fe. Further exemplary materials are provided in U.S. Pat. No. 6,211,598 and International Pub. Nos. WO 2007/024038, each of which is incorporated by reference in its entirety.

Unstretched Materials

The dressings of the invention can include one or more unstretched materials. Such unstretched materials include those having sufficient rigidity to hinder stretching and those having one or more stretchable polymers that are not stretched prior to affixing to a skin region. Exemplary unstretched materials include Tegaderm™, available from 3M, St. Paul, Minn., which can optionally be stretched after affixing to a skin region.

Unstretched materials have not been dimensionally altered and are in a stable dimensional state. Conversely, a stretched material has an unstable dimensional state because the material has been dimensionally altered within the material's elastic region by a force. An unstretched material can also be highly rigid or cross-linked (e.g., highly resistant to stretching). Alternatively, an unstretched material can be a naïve material, which can be stretched in subsequent use.

Exemplary unstretched materials include any polymer or material described herein, a conventional material(s) (e.g., as described herein), permanent adhesive(s), highly cross-linked polymeric material(s), and material(s) with high rigidity or hardness and low ductility (e.g., carboxymethylcellulose, gelatin, pectin, alginate, polyurethane, polymethacrylate, polyvinylpyrrolidone, nylon, polyethylene, polyacrylate, collagen, silicone, polyglycolic acid/polylactic acid, polyglycolic acid, polyglactin, benzyl hyaluronate, or combinations thereof, in any useful form, such as a film, bandage, gel, or hydrogel).

Adhesive Materials

An adhesive can be used within the dressing (e.g., as in the adhesive layer) or used in combination with any method described herein to promote skin tightening.

The adhesive can be a pressure-sensitive adhesive (PSA). The properties of pressure sensitive adhesives are governed by three parameters, tack (initial adhesion), peel strength (adhesion), and shear strength (cohesion). Pressure-sensitive adhesives can be synthesized in several ways, including solvent-borne, water-borne, and hot-melt methods. Tack is the initial adhesion under slight pressure and short dwell time and depends on the adhesive's ability to wet the contact surface. Peel strength is the force required to remove the PSA from the contact surface. The peel adhesion depends on many factors, including the tack, bonding history (e.g. force, dwell time), and adhesive composition. Shear strength is a measure of the adhesive's resistance to continuous stress. The shear strength is influenced by several parameters, including internal adhesion, cross-linking, and viscoelastic properties of the adhesive. Permanent adhesives are generally resistant to debonding and possess very high peel and shear strength.

Exemplary adhesives include a biocompatible matrix (e.g., those including at least one of collagen (e.g., a collagen sponge), low melting agarose (LMA), polylactic acid (PLA), and/or hyaluronicacid (e.g., hyaluranon); a photosensitizer (e.g., Rose Bengal, riboflavin-5-phosphate (R-5-P), methylene blue (MB), N-hydroxypyridine-2-(1H)-thione (N-HTP), a porphyrin, or a chlorin, as well as precursors thereof); a photochemical agent (e.g., 1,8 naphthalimide); a synthetic glue (e.g., a cyanoacrylate adhesive, a polyethylene glycol adhesive, or a gelatin-resorcinol-formaldehyde adhesive); or a biologic sealant (e.g., a mixture of riboflavin-5-phosphate and fibrinogen, a fibrin-based sealant, an albumin-based sealant, or a starch-based sealant). In particular embodiments, the adhesive is biodegradable.

Exemplary pressure-sensitive adhesives include natural rubber, synthetic rubber (e.g., styrene-butadiene and styrene-ethylene copolymers), polyvinyl ether, polyurethane, acrylic, silicones, and ethylene-vinyl acetate copolymers. A copolymer's adhesive properties can be altered by varying the composition (via monomer components) changing the glass transition temperature (Tg) or degree of cross-linking. In general, a copolymer with a lower Tg is less rigid and a copolymer with a higher Tg is more rigid. The tack of PSAs can be altered by the addition of components to alter the viscosity or mechanical properties. Exemplary pressure sensitive adhesives are described in Czech et al., "Pressure-Sensitive Adhesives for Medical Applications," in Wide Spectra of Quality Control, Dr. Isin Akyar (Ed., published by InTech), Chapter 17 (2011), which is hereby incorporated by reference in its entirety In one exemplary technique, a photosensitizer is applied to the tissue (e.g., Rose Bengal (RB) at concentration of less than 1.0% weight per volume in a buffer, e.g., phosphate buffered saline to form a skin tissue-RB complex), and then the tissue is irradiated with electromagnetic energy to produce a seal (e.g., irradiated at a wavelength of at least 488, at less than 2000 J/cm$^2$, and/or at less than 1.5 W/cm$^2$, e.g., about 0.6 W/cm$^2$). This exemplary technique is described in U.S. Pat. No. 7,073,510, which is incorporated by reference in its entirety. In another exemplary technique, a laser can be used for tissue welding. In yet another exemplary technique, a photochemical agent is applied to the tissue, and then the tissue is irradiated with visible light to produce a seal.

Therapeutic Agents

The dressings and methods of the invention can include one or more useful therapeutic agents. Exemplary agents include one or more growth factors (e.g., vascular endothelial growth factor (VEGF), platelet-derived growth factor (PDGF), transforming growth factor beta (TGF-(3), fibroblast growth factor (FGF), epidermal growth factor (EGF), and keratinocyte growth factor); one or more stem cells (e.g., adipose tissue-derived stem cells and/or bone marrow-derived mesenchymal stem cells); steroids (for example, steroids to prevent edema), agents which prevent post-inflammatory skin hyperpigmentation (e.g., hydroquinone, azelaic acid, kojic acid, mandelic acid, or niacinamide); one or more analgesics (e.g., paracetamol/acetaminophen, aspirin, a non-steroidal anti-inflammatory drug, as described herein, a cyclooxygenase-2-specific inhibitor, as described herein, dextropropoxyphene, co-codamol, an opioid (e.g., morphine, codeine, oxycodone, hydrocodone, dihydromorphine, pethidine, buprenorphine, tramadol, or methadone), fentanyl, procaine, lidocaine, tetracaine, dibucaine, benzocaine, p-butylaminobenzoic acid 2-(diethylamino) ethyl ester HCl, mepivacaine, piperocaine, dyclonine, or venlafaxine); one or more antibiotics (e.g., cephalosporin, bacitracin, polymyxin B sulfate, neomycin, bismuth tribromophenate, or polysporin); one or more antifungals (e.g., nystatin); one or more anti-inflammatory agents (e.g., a non-steroidal anti-inflammatory drug (NSAID, e.g., ibuprofen, ketoprofen, flurbiprofen, piroxicam, indomethacin, diclofenac, sulindac, naproxen, aspirin, ketorolac, or tacrolimus), a cyclooxygenase-2-specific inhibitor (COX-2 inhibitor, e.g., rofecoxib (Vioxx®), etoricoxib, and celecoxib (Celebrex®)), a glucocorticoid agent, a specific cytokine directed at T lymphocyte function), a steroid (e.g., a corticosteroid, such as a glucocorticoid (e.g., aldosterone, beclometasone, betamethasone, cortisone, deoxycorticosterone acetate, dexamethasone, fludrocortisone acetate, hydrocortisone, methylprednisolone, prednisone, prednisolone, or triamcinolone) or a mineralocorticoid agent (e.g., aldosterone, corticosterone, or deoxycorticosterone)), or an immune selective anti-inflammatory derivative (e.g., phenylalanine-glutamine-glycine (FEG) and its D-isomeric form (feG))); one or more antimicrobials (e.g., chlorhexidine gluconate, iodine (e.g., tincture of iodine, povidone-iodine, or Lugol's iodine), or silver, such as silver nitrate (e.g., as a 0.5% solution), silver sulfadiazine (e.g., as a cream), or Ag+ in one or more useful carriers (e.g., an alginate, such as Acticoat® including nanocrystalline silver coating in high density polyethylene, available from Smith & Nephew, London, U.K., or Silvercel® including a mixture of alginate, carboxymethylcellulose, and silver coated nylon fibers, available from Systagenix, Gatwick, U.K.; a foam (e.g., Contreet® Foam including a soft hydrophilic polyurethane foam and silver, available from Coloplast A/S, Humlebaak, Denmark); a hydrocolloid (e.g., Aquacel® Ag including ionic silver and a hydrocolloid, available from Conva Tec Inc., Skillman, N.J.); or a hydrogel (e.g., Silvasorb® including ionic silver, available from Medline Industries Inc., Mansfield, Mass.)); one or more antiseptics (e.g., an alcohol, such as ethanol (e.g., 60-90%), 1-propanol (e.g., 60-70%), as well as mixtures of 2-propanol/isopropanol; boric acid; calcium hypochlorite; hydrogen peroxide; manuka honey and/or methylglyoxal; a phenol (carbolic acid) compound, e.g., sodium 3,5-dibromo-4-hydroxybenzene sulfonate, trichlorophenylmethyl iodosalicyl, or triclosan; a polyhexanide compound, e.g., polyhexamethylene biguanide (PHMB); a quaternary ammonium compound, such as benzalkonium chloride (BAC), benzethonium chloride (BZT), cetyl trimethylammonium bromide (CTMB), cetylpyridinium chloride (CPC), chlorhexidine (e.g., chlorhexidine gluconate), or octenidine (e.g., octenidine dihydrochloride); sodium bicarbonate; sodium chloride; sodium hypochlorite (e.g., optionally in combination with boric acid in Dakin's solution); or a triarylmethane dye (e.g., Brilliant Green)); one or more antiproliferative agents (e.g., sirolimus, tacrolimus, zotarolimus, biolimus, or paclitaxel); one or more emollients; one or more hemostatic agents (e.g., collagen, such as microfibrillar collagen, chitosan, calcium-loaded zeolite, cellulose, anhydrous aluminum sulfate, silver nitrate, potassium alum, titanium oxide, fibrinogen, epinephrine, calcium alginate, poly-N-acetyl glucosamine, thrombin, coagulation factor(s) (e.g., II, V, VII, VIII, IX, X, XI, XIII, or Von Willebrand factor, as well as activated forms thereof), a procoagulant (e.g., propyl gallate), an anti-fibrinolytic agent (e.g., epsilon aminocaproic acid or tranexamic acid), and the like); one or more procoagulative agents (e.g., any hemostatic agent described herein, desmopressin, coagulation factor(s) (e.g., II, V, VII, VIII, IX, X, XI, XIII, or Von Willebrand factor, as well as activated forms thereof), procoagulants (e.g., propyl gallate), antifibrinolytics (e.g., epsilon aminocaproic acid), and the like); one or more anticoagulative agents (e.g., heparin or derivatives thereof, such as low molecular weight heparin, fondaparinux, oridraparinux; an anti-platelet agent, such as aspirin, dipyridamole, ticlopidine, clopidogrel, or prasugrel; a factor Xa inhibitor, such as a direct factor Xa inhibitor, e.g., apixaban or rivaroxaban; a thrombin inhibitor, such as a direct thrombin inhibitor, e.g., argatroban, bivalirudin, dabigatran, hirudin, lepirudin, or ximelagatran; or a coumarin derivative or vitamin K antagonist, such as warfarin (coumadin), acenocoumarol, atromentin, phenindione, or phenprocoumon); one or more immune modulators, including corticosteroids and non-steroidal immune modulators (e.g., NSAIDS, such as any described herein); one or more proteins; or one or more vitamins (e.g., vitamin A, C, and/or E).

For the skin tightening methods described herein, the use of anticoagulative and/or procoagulative agents may be of particular relevance. For instance, by controlling the extent of bleeding and/or clotting in the incisions and/or excisions, the skin tightening effect can be more effectively controlled. Thus, in some embodiments, the methods and devices herein include one or more anticoagulative agents, one or more procoagulative agents, one or more hemostatic agents, or combinations thereof. In particular embodiments, the therapeutic agent controls the extent of bleeding and/or clotting in the treated skin region, including the use one or more anticoagulative agents (e.g., to inhibit clot formation prior to skin healing or slit/hole closure) and/or one or more hemostatic or procoagulative agents.

Kits, Optionally Including One or More Applicators

Also described herein are kits for skin tightening or for treating diseases, disorders, and conditions that would benefit from skin restoration or tightening. Accordingly, the present invention includes kits having one or more devices in combination with one or more applicators, as well kits having a combination of two or more devices, where at least one device is a tunable dressing as described herein.

The kit includes a device, such as any tunable dressing described herein, and any other useful component. In some embodiments, the kit includes a device (e.g., a tunable dressing) and an applicator. The applicator can include a frame or any structure configured to affix a device to the skin region, where the frame or structure is optionally disposable. In general, each device or tunable dressing is configured to be affixed to a skin region, and the applicator can be configured to assist in the affixation of such a device. In some embodiments, the applicator maintains the device in an unstretched state to allow for affixing a device having an unstretched layer. In other embodiments, the applicator holds the device to allow for aligning, positioning, and/or placing the device on the desired skin region. In yet other embodiments, the applicator is configured to allow for affixing a tunable dressing immediately after or shortly after forming one or more incisions or excisions in the skin region. In such an embodiment, the applicator is configured to releasably attach to an apparatus for making such an incision or excision (e.g., an apparatus including one or more blades and/or one or more tubes or a microablation tool, such as any described herein). The applicator can be of any useful shape and/or material (e.g., any material or polymer described herein). In some embodiments, the applicator is a frame that provides sufficient support to the device or tunable dressing and/or provides a sterile method to affix the device or tunable dressing. In particular embodiments, the frame includes a rigid plate having one or more view ports (e.g., one or more transparent windows) to allow for positioning of the device. In some embodiments, the frame is structurally configured to attach to an apparatus for making one or more incisions and/or excisions and to release a device (e.g., a tunable dressing) after making such an incision or excision.

In other embodiments, the applicator includes a liner layer having one or more handles, where the liner layer is attached to the proximal surface of a tunable dressing. The handles allow for positioning the dressing over the treated skin region. In some embodiments, the handles are configured to be detached from the dressing immediately prior to or after affixation. In some embodiments, the applicator includes a releasing layer. Exemplary applicators are provided in U.S. Pub. Nos. 2012/0226306 and 2012/0226214, where each is hereby incorporated by reference in its entirety.

There may be a plurality of devices (e.g., tunable dressings) in a kit. Within the kit, the tunable dressings may be packaged individually (e.g., in sets of two or more). In some embodiments, each tunable dressing includes an applicator, where the dressing and the applicator are configured together in one package. In other embodiments, the kit includes one or more tunable dressings in combination with one or more applicators, where each of the dressing(s) and applicator(s) is individually packaged. The dressing(s) and/or applicator(s) are packaged such that they remain sterile until use. In certain embodiments, the dressing(s) and/or applicator(s) are packaged in plastic sheaths. Further, to prevent contamination of the skin region, the dressing(s) and/or applicator(s) are preferably provided for as disposable and/or single-use items.

The kit can include a tunable dressing in combination with any other device or apparatus described herein (e.g., a device or apparatus for forming one or more incisions or excisions in a skin region). In some embodiments, the other device or apparatus includes one or more blades and/or one or more needles. In other embodiments, the other device or apparatus includes a microablation tool. Exemplary microablation tools include a fractional laser microablation tool, a fractional radiofrequency microablation tool, or a fractional ultrasonic microablation tool.

The kit can include any other useful components. Exemplary components include instructions on how to use the device(s), an air blower, a heat gun, a heating pad, one or more therapeutic agents (e.g., any described herein, such as an anticoagulative and/or procoagulative agent, and optionally in combination with a useful dispenser for applying the therapeutic agent, such as a brush, spray, film, ointment, cream, lotion, or gel), one or more wound cleansers (e.g., including any antibiotic, antimicrobial, or antiseptic, such as those described herein, in any useful form, such as a brush, spray, film, ointment, cream, lotion, or gel), one or more debriding agents, and/or other suitable or useful materials.

Methods for Treating Skin Regions

The present invention relates to methods and devices that can be applied to treated skin regions. In particular embodiments, these regions are treated with one or more procedures to improve skin appearance. Accordingly, the devices, dressings, and methods herein can be useful for skin rejuvenation (e.g., removal of pigment, tattoo removal, veins (e.g., spider veins or reticular veins), and/or vessels in the skin) or for treating acne, allodynia, blemishes, ectopic dermatitis, hyperpigmentation, hyperplasia (e.g., lentigo or keratosis), loss of translucency, loss of elasticity, melasma (e.g., epidermal, dermal, or mixed subtypes), photodamage, rashes (e.g., erythematous, macular, papular, and/or bullous conditions), psoriasis, rhytides (or wrinkles, e.g., crow's feet, age-related rhytides, sun-related rhytides, or heredity-related rhytides), sallow color, scar contracture (e.g., relaxation of scar tissue), scarring (e.g., due to acne, surgery, or other trauma), skin aging, skin contraction (e.g., excessive tension in the skin), skin irritation/sensitivity, skin laxity (e.g., loose or sagging skin or other skin irregularities), striae (or stretch marks), vascular lesions (e.g., angioma, erythema, hemangioma, papule, port wine stain, rosacea, reticular vein, or telangiectasia), or any other unwanted skin irregularities.

Such treatments can be include any parts of the body, including the face (e.g., eyelid, cheeks, chin, forehead, lips, or nose), neck, chest (e.g., as in a breast lift), arms, legs, and/or back. Accordingly, the devices on the invention can be arranged or configured to be amenable to the size or geometry of different body regions. Such arrangements and configurations can include any useful shape (e.g., linear, curved, or stellate), size, and/or depth.

In one exemplary procedure, a plurality of tissue portions are incised into or excised from a skin region in a subject (e.g., about 2, 3, 4, 5, 6, 7, 8, 9, 10, 15, 20, 25, 30, 35, 40, 45, 50, 75, 100, or more tissue portions, such as between about 2 and 100 tissue portions (e.g., between 2 and 10, 2 and 15, 2 and 20, 2 and 25, 2 and 30, 2 and 35, 2 and 40, 2 and 45, 2 and 50, 2 and 75, 5 and 10, 5 and 15, 5 and 20, 5 and 25, 5 and 30, 5 and 35, 5 and 40, 5 and 45, 5 and 50, 5 and 75, 5 and 100, 10 and 20, 10 and 25, 10 and 30, 10 and 35, 10 and 40, 10 and 45, 10 and 50, 10 and 75, 10 and 100, 15 and 20, 15 and 25, 15 and 30, 15 and 35, 15 and 40, 15 and 45, 15 and 50, 15 and 75, 15 and 100, 20 and 25, 20 and 30, 20 and 35, 20 and 40, 20 and 45, 20 and 50, 20 and 75, 20 and 100, 25 and 30, 25 and 35, 25 and 40, 25 and 45, 25 and 50, 25 and 75, 25 and 100, 30 and 35, 30 and 40, 30 and 45, 30 and 50, 30 and 75, 30 and 100, 35 and 40, 35 and 45, 35 and 50, 35 and 75, 35 and 100, 40 and 45, 40 and 50, 40 and 75, 40 and 100, 50 and 75, or 50 and 100)). Such tissue portions can be included in any useful geometric, non-geometric, or random array (e.g., such as those described herein for an array of tubes and/or blades). Such tissue portions can have any useful dimension that promotes wound or skin healing. Non-limiting dimensions of a tissue portion includes at least one dimension that is less than about 2.0 mm (e.g., less than or equal to about 1.5 mm, 1 mm, 0.75 mm, 0.5 mm, 0.3 mm, 0.2 mm, 0.1 mm, 0.075 mm, 0.05 mm, or 0.025 mm) or between about 0.025 mm and 2.0 mm (e.g., between about 0.025 mm and 1.5 mm, 0.025 mm and 1.0 mm, 0.025 mm and 0.75 mm, 0.025 mm and 0.5 mm, 0.025 mm and 0.3 mm, 0.025 mm and 0.2 mm, 0.025 mm and 0.1 mm, 0.025 mm and 0.075 mm, 0.025 mm and 0.05 mm, 0.05 mm and 2.0 mm, 0.05 mm and 1.5 mm, 0.05 mm and 1.0 mm, 0.05 mm and 0.75 mm, 0.05 mm and 0.5 mm, 0.05 mm and 0.3 mm, 0.05 mm and 0.2 mm, 0.05 mm and 0.1 mm, 0.05 mm and 0.075 mm, 0.075 mm and 2.0 mm, 0.075 mm and 1.5 mm, 0.075 mm and 1.0 mm, 0.075 mm and 0.75 mm, 0.075 mm and 0.5 mm, 0.075 mm and 0.3 mm, 0.075 mm and 0.2 mm, 0.075 mm and 0.1 mm, 0.1 mm and 2.0 mm, 0.1 mm and 1.5 mm, 0.1 mm and 1.0 mm, 0.1 mm and 0.75 mm, 0.1 mm and 0.5 mm, 0.1 mm and 0.3 mm, 0.1 mm and 0.2 mm, 0.2 mm and 2.0 mm, 0.2 mm and 1.5 mm, 0.2 mm and 1.0 mm, 0.2 mm and 0.75 mm, 0.2 mm and 0.5 mm, 0.2 mm and 0.3 mm, 0.3 mm and 2.0 mm, 0.3 mm and 1.5 mm, 0.3 mm and 1.0 mm, 0.3 mm and 0.75 mm, 0.3 mm and 0.5 mm, 0.5 mm and 2.0 mm, 0.5 mm and 1.5 mm, 0.5 mm and 1.0 mm, 0.5 mm and 0.75 mm, 0.75 mm and 2.0 mm, 0.75 mm and 1.5 mm, or 0.75 mm and 1.0 mm).

In some embodiments, the incised or excised tissue portions forms a hole in the skin region, where the diameter or width of the hole is less than about 1.0 mm and results in a tissue portion having a diameter or width that is less than about 1.0 mm. In further embodiments, the tissue portion has a diameter or width that is less than about 1.0 mm and a length of more than about 1.0 mm (e.g., about 1.0 mm, 1.5 mm, 2.0 mm. 2.5 mm, 3.0 mm, or 3.5 mm). In particular embodiments, relatively small dimensions of the tissue portions can promote healing while minimizing the formation of scars.

In other embodiments, the incised or excised tissue portions forms a slit in the skin region, where the length or width of the slit is less than about 1.0 mm and results in a tissue portion having a length or width that is less than about 1.0 mm. In further embodiments, the tissue portion has a length or width that is less than about 1.0 mm and a length of more than about 1.0 mm (e.g., about 1.0 mm, 1.5 mm, 2.0 mm. 2.5 mm, 3.0 mm, or 3.5 mm). In particular embodiments, relatively small dimensions of the tissue portions can promote healing while minimizing the formation of scars.

The tissue portion can be of any useful shape. Exemplary shapes include cylinders (i.e., thereby forming round or elongated holes in the skin region), holes (e.g., microholes), slits (e.g., microslits), elongated strips (i.e., thereby forming elongated openings in the skin region), or other geometries including at least dimension that is less than about 1.0 mm (e.g., less than or equal to about 0.75 mm, about 0.5 mm, about 0.3 mm, about 0.2 mm, about 0.1 mm, or about 0.05 mm) or between about 0.05 mm and 1.0 mm (e.g., 0.05 mm and 0.75 mm, 0.05 mm and 0.5 mm, 0.05 mm and 0.3 mm, 0.05 mm and 0.2 mm, 0.05 mm and 0.1 mm, 0.1 mm and 1.0 mm, 0.1 mm and 0.75 mm, 0.1 mm and 0.5 mm, 0.1 mm and 0.3 mm, 0.1 mm and 0.2 mm, 0.2 mm and 1.0 mm, 0.2 mm and 0.75 mm, 0.2 mm and 0.5 mm, 0.2 mm and 0.3 mm, 0.3 mm and 1.0 mm, 0.3 mm and 0.75 mm, 0.3 mm and 0.5 mm, 0.4 mm and 1.0 mm, 0.4 mm and 0.75 mm, 0.4 mm and 0.5 mm, 0.5 mm and 1.0 mm, 0.5 mm and 0.75 mm, 0.6 mm and 1.0 mm, 0.6 mm and 0.75 mm, or 0.75 mm and 1.0 mm). In other embodiments, the incised tissue portion and/or excised tissue portion has an areal dimension (e.g., a cross-sectional dimension in the xy-plane, such as an areal dimension of a circle or non-circular (e.g., elliptical) shape) of less than about or equal to about 1.0 $mm^2$ (e.g., less than or equal to about 0.9 $mm^2$, 0.8 $mm^2$, 0.7 $mm^2$, 0.6 $mm^2$, 0.5 $mm^2$, 0.4 $mm^2$, 0.3 $mm^2$, 0.2 $mm^2$, 0.1 $mm^2$, 0.07 $mm^2$, 0.05 $mm^2$, 0.03 $mm^2$, 0.02 $mm^2$, 0.01 $mm^2$, 0.007 $mm^2$, 0.005 $mm^2$, 0.003 $mm^2$, 0.002 $mm^2$, or 0.001 $mm^2$) or between about 0.001 $mm^2$ and 1.0 $mm^2$ (e.g., 0.001 $mm^2$ and 0.9 $mm^2$, 0.001 $mm^2$ and 0.8 $mm^2$, 0.001 $mm^2$ and 0.7 $mm^2$, 0.001 $mm^2$ and 0.6 $mm^2$, 0.001 $mm^2$ and 0.5 $mm^2$, 0.001 $mm^2$ and 0.4 $mm^2$, 0.001 $mm^2$ and 0.3 $mm^2$, 0.001 $mm^2$ and 0.2 $mm^2$, 0.001 $mm^2$ and 0.1 $mm^2$, 0.001 $mm^2$ and 0.07 $mm^2$, 0.001 $mm^2$ and 0.05 $mm^2$, 0.001 $mm^2$ and 0.03 $mm^2$, 0.001 $mm^2$ and 0.02 $mm^2$, 0.001 $mm^2$ and 0.01 $mm^2$, 0.001 $mm^2$ and 0.007 $mm^2$, 0.001 $mm^2$ and 0.005 $mm^2$, 0.001 $mm^2$ and 0.003 $mm^2$, 0.001 $mm^2$ and 0.002 $mm^2$, 0.002 $mm^2$ and 1.0 $mm^2$, 0.002 $mm^2$ and 0.9 $mm^2$, 0.002 $mm^2$ and 0.8 $mm^2$, 0.002 $mm^2$ and 0.7 $mm^2$, 0.002 $mm^2$ and 0.6 $mm^2$, 0.002 $mm^2$ and 0.5 $mm^2$, 0.002 $mm^2$ and 0.4 $mm^2$, 0.002 $mm^2$ and 0.3 $mm^2$, 0.002 $mm^2$ and 0.2 $mm^2$, 0.002 $mm^2$ and 0.1 $mm^2$, 0.002 $mm^2$ and 0.07 $mm^2$, 0.002 $mm^2$ and 0.05 $mm^2$, 0.002 $mm^2$ and 0.03 $mm^2$, 0.002 $mm^2$ and 0.02 $mm^2$, 0.002 $mm^2$ and 0.01 $mm^2$, 0.002 $mm^2$ and 0.007 $mm^2$, 0.002 $mm^2$ and 0.005 $mm^2$, 0.002 $mm^2$ and 0.003 $mm^2$, 0.005 $mm^2$ and 1.0 $mm^2$, 0.005 $mm^2$ and 0.9 $mm^2$, 0.005 $mm^2$ and 0.8 $mm^2$, 0.005 $mm2$ and 0.7 $mm^2$, 0.005 $mm^2$ and 0.6 $mm^2$, 0.005 $mm^2$ and 0.5 $mm^2$, 0.005 $mm^2$ and 0.4 $mm^2$, 0.005 $mm^2$ and 0.3 $mm^2$, 0.005 $mm^2$ and 0.2 $mm^2$, 0.005 $mm^2$ and 0.1 $mm^2$, 0.005 $mm^2$ and 0.07 $mm^2$, 0.005 $mm^2$ and 0.05 $mm^2$, 0.005 $mm^2$ and 0.03 $mm^2$, 0.005 $mm^2$ and 0.02 $mm^2$, 0.005 $mm^2$ and 0.01 $mm^2$, 0.005 $mm^2$ and 0.007 $mm^2$, 0.007 $mm^2$ and 1.0 $mm^2$, 0.007 $mm^2$ and 0.9 $mm^2$, 0.007 $mm^2$ and 0.8 $mm^2$, 0.007 $mm^2$ and 0.7 $mm^2$, 0.007 $mm^2$ and 0.6 $mm^2$, 0.007 $mm^2$ and 0.5 $mm^2$, 0.007 $mm^2$ and 0.4 $mm^2$, 0.007 $mm^2$ and 0.3 $mm^2$, 0.007 $mm^2$ and 0.2 $mm^2$, 0.007 $mm^2$ and 0.1 $mm^2$, 0.007 $mm^2$ and 0.07 $mm^2$, 0.007 $mm^2$ and 0.05 $mm^2$, 0.007 $mm^2$ and 0.03 $mm^2$, 0.007 $mm^2$ and 0.02 $mm^2$, 0.007 $mm^2$ and 0.01 $mm^2$, 0.01 $mm^2$ and 1.0 $mm^2$, 0.01 $mm^2$ and 0.9 $mm^2$, 0.01 $mm^2$ and 0.8 $mm^2$, 0.01 $mm^2$ and 0.7 $mm^2$, 0.01 $mm^2$ and 0.6 $mm^2$, 0.01 $mm^2$ and 0.5 $mm^2$, 0.01 $mm^2$ and 0.4 $mm^2$, 0.01 $mm^2$ and 0.3 $mm^2$, 0.01 $mm^2$ and 0.2 $mm^2$, 0.01 $mm^2$ and 0.1 $mm^2$, 0.01 $mm^2$ and 0.07 $mm^2$, 0.01 $mm^2$ and 0.05 $mm^2$, 0.01 $mm^2$ and 0.03 $mm^2$, 0.01 $mm^2$ and 0.02 $mm^2$, 0.03 $mm^2$ and 1.0 $mm^2$, 0.03 $mm^2$ and 0.9 $mm^2$, 0.03 $mm^2$ and 0.8 $mm^2$, 0.03 $mm^2$ and 0.7 $mm^2$, 0.03 $mm^2$ and 0.6 $mm^2$, 0.03 $mm^2$ and 0.5 $mm^2$, 0.03 $mm^2$ and 0.4 $mm^2$, 0.03 $mm^2$ and 0.3 $mm^2$, 0.03 $mm^2$ and 0.2 $mm^2$, 0.03 $mm^2$ and 0.1 $mm^2$, 0.03 $mm^2$ and 0.07 $mm^2$, 0.03 $mm^2$ and 0.05 $mm^2$, 0.07 $mm^2$ and 1.0 $mm^2$, 0.07 $mm^2$ and 0.9 $mm^2$, 0.07 $mm^2$ and 0.8 $mm^2$, 0.07 $mm^2$ and 0.7 $mm^2$, 0.07 $mm^2$ and 0.6 $mm^2$, 0.07 $mm^2$ and 0.5 $mm^2$, 0.07 $mm^2$ and 0.4 $mm^2$, 0.07 $mm^2$ and 0.3 $mm^2$, 0.07 $mm^2$ and 0.2 $mm^2$, 0.07 $mm^2$ and 0.1 $mm^2$, 0.1 $mm^2$ and 1.0 $mm^2$, 0.1 $mm^2$ and 0.9 $mm^2$, 0.1 $mm^2$ and 0.8 $mm^2$, 0.1 $mm^2$ and 0.7 $mm^2$, 0.1 $mm^2$ and 0.6 $mm^2$, 0.1 $mm^2$ and 0.5 $mm^2$, 0.1 $mm^2$ and 0.4 $mm^2$, 0.1 $mm^2$ and 0.3 $mm^2$, 0.1 $mm^2$ and 0.2 $mm^2$, 0.3 $mm^2$ and 1.0 $mm^2$, 0.3 $mm^2$ and 0.9 $mm^2$, 0.3 $mm^2$ and 0.8 $mm^2$, 0.3 $mm^2$ and 0.7 $mm^2$, 0.3 $mm^2$ and 0.6 $mm^2$, 0.3 $mm^2$ and 0.5 $mm^2$, 0.3 $mm^2$ and 0.4 $mm^2$, 0.5 $mm^2$ and 1.0 $mm^2$, 0.5 $mm^2$ and 0.9 $mm^2$, 0.5 $mm^2$ and 0.8 $mm^2$, 0.5 $mm^2$ and 0.7 $mm^2$, 0.5 $mm^2$ and 0.6 $mm^2$, 0.7 $mm^2$ and 1.0 $mm^2$, 0.7 $mm^2$ and 0.9 $mm^2$, or 0.7 $mm^2$ and 0.8 $mm^2$). When viewed from the top of the skin (i.e., along the z-direction, as shown in FIG. 1A, or within the xy-plane of the skin, as shown in FIGS. 3A-3C), the shape of the hole can be circular or non-circular (e.g., elliptical). Exemplary shapes of tissue portions are provided in FIGS. 1A-1C and 3A-3C and its associated text of U.S. Pub. No. 2012/0041430, which are hereby incorporated by reference in its entirety Any beneficial areal fraction of the skin region can be removed, such as an areal fraction of less than about 70% (e.g., less than about 65%, 60%, 55%, 50%, 45%, 40%, 35%, 30%, 25%, 20%, 10%, or 5%) or such as between about 5% and 80% (e.g., between about 5% and 10%, 5% and 10%, 5% and 20%, 5% and 25%, 5% and 30%, 5% and 35%, 5% and 40%, 5% and 45%, 5% and 50%, 5% and 55%, 5% and 60%, 5% and 65%, 5% and 70%, 5% and 75%, 10% and 10%, 10% and 20%, 10% and 25%, 10% and 30%, 10% and 35%, 10% and 40%, 10% and 45%, 10% and 50%, 10% and 55%, 10% and 60%, 10% and 65%, 10% and 70%, 10% and 75%, 10% and 80%, 15% and 20%, 15% and 25%, 15% and 30%, 15% and 35%, 15% and 40%, 15% and 45%, 15% and 50%, 15% and 55%, 15% and 60%, 15% and 65%, 15% and 70%, 15% and 75%, 15% and 80%, 20% and 25%, 20% and 30%, 20% and 35%, 20% and 40%, 20% and 45%, 20% and 50%, 20% and 55%, 20% and 60%, 20% and 65%, 20% and 70%, 20% and 75%, or 20% and 80%).

Furthermore, the plurality of tissue portions can be incised or excised in any beneficial pattern within the skin region. Exemplary patterns within the skin region include tile patterns or fractal-like shapes, where the array of hollow tubes can be arranged, e.g., in a base, to effectuate such a pattern. For example, a higher density and/or smaller spacing of tissue portions (e.g., slits and/or holes) can be incised or excised in the skin in center of the pattern or in thicker portions of the skin. In another example, the pattern within the skin can be random, staggered rows, parallel rows, a circular pattern, a spiral pattern, a square or rectangular pattern, a triangular pattern, a hexagonal pattern, a radial distribution, or a combination of one or more such patterns of the incised or excised tissue portions. The pattern can arise from modifications to the average length, depth, or width of an incised or excised tissue portion, as well as the density, orientation, and spacing between such incisions and/or excisions (e.g., by using an apparatus having one or more blades or tubes with differing lengths, widths, or geometries that are arranged in a particular density or spacing pattern). Such patterns can be optimized to promote unidirectional, non-directional, or multidirectional contraction or expansion of skin (e.g., in the x-direction, y-direction, x-direction, x-y plane, y-z plane, x-z plane, and/or xyz-plane), such as by modifying the average length, depth, width, density, orientation, and/or spacing between incisions and/or excisions.

Any useful portion of the skin can be incised or excised. Such tissue portions can include epidermal tissue, dermal tissue, and/or cells or tissue proximal to the dermal/fatty layer boundary (e.g., stem cells). In particular embodiments, the incised or excised tissue portions forms a hole in the skin region, where the depth of the hole is more than about 1.0 mm and results in a tissue portion having a length that is more than about 1.0 mm (e.g., about 1.0 mm, 1.5 mm, 2.0 mm. 2.5 mm, 3.0 mm, or 3.5 mm). In particular embodiments, the incised or excised tissue portions forms a slit in the skin region, where the depth of the slit is more than about 1.0 mm and results in a tissue portion having a length that is more than about 1.0 mm (e.g., about 1.0 mm, 1.5 mm, 2.0 mm. 2.5 mm, 3.0 mm, or 3.5 mm). In some embodiments, the tissue portion has a length that corresponds to a typical total depth of the skin layer (e.g., epidermal and dermal layers). Based on the part of the body, the total depth of the epidermal and dermal layers can vary. In some embodiments, the depth of the epidermal layer is between about 0.8 mm to 1.4 mm, and/or the depth of the dermal layer is between about 0.3 mm to 4.0 mm. In other embodiments, the total depth of the skin layer (e.g., epidermal and dermal layers) is between about 1.0 mm and 5.5 mm, thereby resulting in a tissue portion having a length between about 1.0 mm and 5.5 mm (e.g., between about 1.0 mm and 1.5 mm, 1.0 mm and 2.0 mm, 1.0 mm and 2.5 mm, 1.0 mm and 3.0 mm, 1.0 mm and 3.5 mm, 1.0 mm and 4.0 mm, 1.0 mm and 4.5 mm, 1.0 mm and 5.0 mm, 1.5 mm and 2.0 mm, 1.5 mm and 2.5 mm, 1.5 mm and 3.0 mm, 1.5 mm and 3.5 mm, 1.5 mm and 4.0 mm, 1.5 mm and 4.5 mm, 1.5 mm and 5.0 mm, 1.5 mm and 5.5 mm, 2.0 mm and 2.5 mm, 2.0 mm and 3.0 mm, 2.0 mm and 3.5 mm, 2.0 mm and 4.0 mm, 2.0 mm and 4.5 mm, 2.0 mm and 5.0 mm, 2.0 and 5.5 mm, 2.5 mm and 3.0 mm, 2.5 mm and 3.5 mm, 2.5 mm and 4.0 mm, 2.5 mm and 4.5 mm, 2.5 mm and 5.0 mm, 2.5 mm and 5.5 mm, 3.0 mm and 3.5 mm, 3.0 mm and 4.0 mm, 3.0 mm and 4.5 mm, 3.0 mm and 5.0 mm, 3.0 and 5.5 mm, 3.5 mm and 4.0 mm, 3.5 mm and 4.5 mm, 3.5 mm and 5.0 mm, 3.5 and 5.5 mm, 4.0 mm and 4.5 mm, 4.0 mm and 5.0 mm, 4.0 and 5.5 mm, 4.5 mm and 5.0 mm, 4.5 and 5.5 mm, or 5.0 mm and 5.5 mm). In yet other embodiments, the average total depth of the tissue portion or the skin layer (e.g., epidermal and dermal layers) is about 1.5 mm. In yet other embodiments, the average total depth of the tissue portion or the skin layer (e.g., epidermal and dermal layers) is about 3 mm. In further embodiments, the tissue portion does not include a significant amount of subcutaneous tissue, and any apparatus described herein can be optimized (e.g., with one or more stop arrangements) to control the depth of the incision or excision and/or the length of the incised or excised tissue portions.

Incisions can be performed by any useful procedure or component. For example, a plurality of incised tissue portions can be achieved by use of an ablative laser (e.g., an ablative $CO_2$ laser (about 10600 nm), a superficial fractional $CO_2$ laser, a fractional Er:YAG laser (about 2940 nm), a fractional Er:YSGG laser (about 2790 nm), an Nd-YAG laser (about 1320 nm), a mid-IR fractional photothermolysis laser, or a fractional deep dermal ablation $CO_2$ laser), an ultrasonic apparatus, a non-coherent light source, a radiofrequency source, or a plurality of blades (e.g., substantially parallel blades). In some embodiments, the one or more blades can include connected, adjacent blades to provide narrow, elongated openings (or slits) in the skin region. Exemplary procedures and apparatuses including one or more blades are described in FIGS. 3, 4, 5A-5B, 6A-6B, 7A-7C, 8A-8C, 9, 10, 11A-11B, 14, 15A-15B, and 16A-16D and its associated text in U.S. Pub. No. 2011/0251602, which are incorporated herein by reference.

Excisions can be performed by any useful procedure or component. For example, a plurality of excised tissue portions can be achieved by use of one or more hollow tubes or needles (e.g., where the inner diameter of at least one tube is less than about 0.5 mm, about 0.3 mm, or about 0.2 mm) or one or more solid tubes or needles. Exemplary components for performing excisions include a needle (e.g., a 16 gauge needle having an inner diameter of 1.194 mm; an 18 gauge needle having an inner diameter of 0.838 mm; a 20 gauge needle having an inner diameter of 0.564 mm; a 23 gauge needle having an inner diameter of about 0.337 mm and an outer diameter of about 0.51 mm, thereby resulting in a tissue portion having a dimension (e.g., a width or diameter) of about 0.3 mm; a 25 gauge needle having an inner diameter of about 0.26 mm or a thin-walled 25 gauge needle having an inner diameter of about 0.31 mm and an outer diameter of about 0.51 mm, thereby resulting in a tissue portion having a dimension (e.g., a width or diameter) of about 0.2 mm; a 30 gauge needle having an inner diameter of about 0.159 mm; a 32 gauge needle having an inner diameter of about 0.108 mm; or a 34 gauge needle having an inner diameter of about 0.0826 mm), where such needles can be a hollow biopsy needle or a solid needle; one or more microaugers; or one or more microabraders.

The geometry of the one or more tubes can include at least two points (or prongs) (e.g., at least three, four, five, six, seven, eight, or more points) provided at a distal end of the tube (e.g., to facilitate separation of the tissue portions from the surrounding tissue and/or insertion of the tubes into the skin region), where an angle formed by at least one of the points is about thirty degrees. Exemplary tubes include those having two points (e.g., by grinding in orientations that are 180 degrees apart), three points (e.g., by grinding in orientations that are 120 degrees apart), or four points (e.g., by grinding in orientations that are 90 degrees apart). The points can optionally include a beveled edge (e.g., to further facilitate separation of tissue portions or insertion of tubes).

The points can have any useful geometric configuration. In one example, the tube has a longitudinal axis (i.e., along the length of the tube) and a diameter (i.e., through the cross-section of the tube), as well as a proximal end and the distal end. The distal end can include one or more points, where each point is characterized by angle a (i.e., the angle between each of the opposing lateral sides of the tube that forms the point and the longitudinal axis of the tube). When viewed from the side, the angle formed by a point is characterized by angle $2a$. For example, a tip angle of about 30 degrees corresponds to an angle a of about 15 degrees. Furthermore, the angled distal end of the tube can be formed (e.g., by grinding or cutting) at angle a, e.g., to form a second bevel structure at the distal end of a tube, where this second bevel is characterized by angle r3 and is orthogonal to the primary point (or bevel) characterized by angle a. This second bevel can be provided to reduce the size or width of the point. Exemplary angle a and p includes less than about 20 degrees, 15 degrees, 10, degrees, or 5 degrees (e.g., about 15 degrees, 10 degrees, 6 degrees, 5 degrees, or 3 degrees). See, e.g., FIGS. 8A-8J and its associated text of U.S. Pub. No. 2011/0313429, which are hereby incorporated by reference in its entirety, for exemplary points, angle a, and angle [3.

The tubes can optionally include one or more notches within the lumen of the needle (i.e., if the tube is hollow) and/or extensions on the exterior surface of the needle (e.g., at the distal portion of the needle). Such notches and extensions could be useful to promote cutting of tissue surrounding the incised or excised tissue portions. Exemplary needles having such notches and/or extensions include a microauger, as well as any needles provided in FIGS. 5A-5E and described its associated text of International Pub. No. WO 2012/103492, which are hereby incorporated by reference in its entirety, for apparatuses having notches and/or extensions.

The tubes can optionally include one or more protrusions or barbs within the lumen of the needle (i.e., if the tube is hollow) to promote retention of fat within the needle. In use, an apparatus including such tubes can be inserted into the subcutaneous fat layer and then withdrawn to remove retained fat tissue. See, e.g., FIGS. 1A-1C, 2A-2C, 3A, 4, 5A-5C, 6A-6B, 7, and 8A-8C and its associated text of International Pub. No. WO 2013/013196, which are hereby incorporated by reference in its entirety, for apparatuses having protrusions or barbs.

The components for making incisions and/or excisions (e.g., blades and/or tubes) can be provided in any useful arrangement (e.g., a linear array, a radial array, or any described herein) of one or more components (e.g., two, three, four, five, ten, thirty, fifty, hundred, or more). The spacing between each component (e.g., blade and/or tube) can be of any useful dimension, such as between about 1 mm and 50 mm (e.g., between about 1 mm and 40 mm, 1 mm and 30 mm, 1 mm and 25 mm, 1 mm and 20 mm, 1 mm and 15 mm, 1 mm and 10 mm, 1 mm and 5 mm, 1 mm and 3 mm, 3 mm and 50 mm, 3 mm and 40 mm, 3 mm and 30 mm, 3 mm and 25 mm, 3 mm and 20 mm, 3 mm and 15 mm, 3 mm and 10 mm, 3 mm and 5 mm, 5 mm and 50 mm, 5 mm and 40 mm, 5 mm and 30 mm, 5 mm and 25 mm, 5 mm and 20 mm, 5 mm and 15 mm, 5 mm and 10 mm, 10 mm and 50 mm, 10 mm and 40 mm, 10 mm and 30 mm, 10 mm and 25 mm, 10 mm and 20 mm, 10 mm and 15 mm, 15 mm and 50 mm, 15 mm and 40 mm, 15 mm and 30 mm, 15 mm and 25 mm, 15 mm and 20 mm, 20 mm and 50 mm, 20 mm and 40 mm, 20 mm and 30 mm, 20 mm and 25 mm, 30 mm and 50 mm, 30 mm and 40 mm, or 40 mm and 50 mm). Such arrangements can include one or more tubes and/or blades (e.g., about 2, 3, 4, 5, 6, 7, 8, 9, 10, 15, 20, 25, 30, 35, 40, 45, 50, 75, 100, or more tubes and/or blades, such as between about 2 and 100 tubes and/or blades (e.g., between 2 and 10, 2 and 15, 2 and 20, 2 and 25, 2 and 30, 2 and 35, 2 and 40, 2 and 45, 2 and 50, 2 and 75, 5 and 10, 5 and 15, 5 and 20, 5 and 25, 5 and 30, 5 and 35, 5 and 40, 5 and 45, 5 and 50, 5 and 75, 5 and 100, 10 and 20, 10 and 25, 10 and 30, 10 and 35, 10 and 40, 10 and 45, 10 and 50, 10 and 75, 10 and 100, 15 and 20, 15 and 25, 15 and 30, 15 and 35, 15 and 40, 15 and 45, 15 and 50, 15 and 75, 15 and 100, 20 and 25, 20 and 30, 20 and 35, 20 and 40, 20 and 45, 20 and 50, 20 and 75, 20 and 100, 25 and 30, 25 and 35, 25 and 40, 25 and 45, 25 and 50, 25 and 75, 25 and 100, 30 and 35, 30 and 40, 30 and 45, 30 and 50, 30 and 75, 30 and 100, 35 and 40, 35 and 45, 35 and 50, 35 and 75, 35 and 100, 40 and 45, 40 and 50, 40 and 75, 40 and 100, 50 and 75, or 50 and 100)).

Such arrangements of components can be any of various two-dimensional or three-dimensional patterns along a base holding one or more components for making incisions and/or excisions (e.g., blades and/or tubes). The base can be optionally mounted on a roller apparatus having a cylindrical body with a longitudinal rotational axis, where the one or more blades and/or tubes are arranged on the longitudinal surface of the cylindrical body. In some embodiments, the blade or tube extends as substantially coplanar extensions of the cylindrical body. In use, rotation of the cylindrical body along the skin results in the incision or excision of tissue portions by the blade or tubes. Exemplary roller apparatuses are provided in FIGS. 11A-11B and its associated text in U.S. Pub. No. 2011/0251602, in FIGS. 3A-3B and its associated text in International Pub. No. WO 2012/103492, which are hereby incorporated by reference in its entirety.

Such components for making incisions and/or excisions (e.g., blades and/or tubes) can include one or more stop arrangements (e.g., one or more collars, which can be coupled to the blade to allow for adjustment along the long axis of the blade or which can be coupled to the outer portion of the tube and be adjusted along the long axis of the tube to control the depth of incision or excision in the biological tissue); one or more sleeves around a portion of a blade and/or a tube, such that the sleeve is slidably translatable along the longitudinal axis of the tube or blade (e.g., to incise or excise tissue portions below the surface of the skin region); a vibrating arrangement (e.g., a piezoelectric element, a solenoid, a pneumatic element, or a hydraulic element) that mechanically couples to at least one blade or hollow tube (e.g., to promote insertion of one or more blades or tubes into the skin region, such as by providing an amplitude of vibration in the range of about 50-500 pm (e.g., between about 100-200 pm) or by providing a frequency of the induced vibrations to be between about 10 Hz and about 10 kHz (e.g., between about 500 Hz and about 2 kHz, or even about 1 kHz)); a suction or pressure system (e.g., by squeezing a flexible bulb or deformable membrane attached thereto or by opening a valve leading from a source of elevated pressure, such as a small pump) to stabilize the surrounding skin region prior to incision or excision and/or to facilitate removal of the skin portions from the tube; a pin within the lumen to the tube to facilitate removal of the skin portions from the tube; one or more actuators for positioning, translating, and/or rotating the one or more blades and/or tubes relative to the skin portion or relative to the optional one or more pins; a housing or frame to stabilize the surrounding skin region prior to incision or excision; one or more actuators for positioning and/or translating the one or more pins relative to the skin portion or relative to one or more tubes; one or more sensors (e.g., force sensors, optical sensors, laser fibers, photodetectors, and/or position sensors) in communication with one or more tubes, blades, pins, actuators, valves, or pressure systems to detect the position of the tubes or pins, the presence of a tissue portion in the tube, the position of the apparatus relative to the treated skin portion; a reciprocating arrangement attached to a base or a substrate having one or more attached blades or tubes (e.g., a motor or actuator configured to repeatedly insert and/or withdrawn one or more blades or tubes); a fluid system coupled to the blades and/or tubes to facilitate removal of incised or excised tissue portions or to irrigate the skin portion, e.g., with saline or a phosphate buffered solution; a heat source (e.g., a resistive heater or current) in communication with the blade and/or tube to promote cauterization or ablation of tissue portions; an optical element (e.g., a lens, a prism, a reflector, etc.) to facilitate viewing of the skin portion beneath the apparatus, tube, or blade; and/or an abrading element optionally mounted on a rotating shaft (e.g., to promote dermabrasion).

Exemplary blades, tubes, pins, apparatuses, and methods are provided in FIGS. 5A-5B, 6A-6C, 7, and 8A-8B and its associated text of U.S. Pub. No. 2012/0041430; in FIGS. 8A-8J, 10A-10B, 11, 12, 13A-13B, 14, and 15A-15E and its associated text of U.S. Pub. No. 2011/0313429; in FIGS. 3, 4, 5A-5B, 6A-6B, 7A-7C, 8A-8C, 9, 10, 11A-11B, 14, 15A-15B, and 16A-D and its associated text in U.S. Pub. No. 2011/0251602; in FIGS. 1A-1B, 2A-2C, 3A-3B, 4A-4B, 5A-5E, and 6 and its associated text in International Pub. No. WO 2012/103492; in FIGS. 1, 2, 3, and 4 and its associated text in International Pub. No. WO 2012/103483; in FIGS. 1, 3, and 4 and its associated text in International Pub. No. WO 2012/103488; in FIGS. 1A-1C, 2A-2C, 3A, 4, 5A-5C, 6A-6B, 7, and 8A-8C and its associated text of International Pub. No. WO 2013/013196; in FIGS. 1, 2A-2D, 3, and 4 and its associated text of International Pub. No. WO 2013/013199, which are hereby incorporated by reference in its entirety.

The tubes, blades, pins, and apparatuses can be formed from any useful material and optionally coated or chemically treated to promote incision or excision of a tissue portion and/or to increase precision or effectiveness for treating the skin region. Exemplary materials include metal (e.g., a stainless steel tube, 304 stainless steel, a surgical stainless steel), a biopsy needle, an epoxy, a glass, a polymer, a plastic, a resin, another structurally rigid material, or a similar structure. Exemplary coatings include a lubricant, a low-friction material (e.g., Teflon™), a chromium coating (e.g., ME-92TM, such as to increase material strength), a plastic, a polymer (e.g., nylon or polyethylene), a polished metal alloy, or the like.

In particular embodiments, an apparatus for treating skin includes at least one hollow tube including at least two points provided at a distal end thereof and an optional stop arrangement coupled to the outer portion of the tube (e.g., to control and/or limit a distance to which the one tube is inserted into a biological tissue), where the angle formed by at least one of the points is about thirty degrees, where the inner diameter of at least one tube is less than about 1 mm, and where at least one section of the hollow tube is structured to be inserted into a biological tissue to incise or excise at least one tissue therefrom when the tube is withdrawn from the tissue. In other embodiments, the apparatus further includes a pin provided at least partially within the central lumen of a tube, where the pin is controllably translatable in a direction along a longitudinal axis of the one tube and the pin is configured to facilitate removal of at least one tissue portion from the tube. In another embodiment, the apparatus for treating skin includes a plurality of cutting arrangements (e.g., blades) structured to form a plurality of spaced-apart micro-slits (e.g., openings) in tissue, where each of the micro-slits has a length of extension along a surface of the tissue that is less than about 2 mm. In other embodiments, the apparatus includes at least one hollow tube (e.g., needle) configured to be at least partially inserted into a biological tissue; at least one opening provided on a wall of the hollow tube; at least one cutting edge protruding from the wall of the hollow tube proximal to the at least one opening; and a sleeve provided around at least a portion of the tube and configured to be translatable along a longitudinal axis of the tube, where a distance from the longitudinal axis of the tube to an outer edge of the sleeve is at least as large as a distance from the longitudinal axis of the tube to an outer portion of the cutting edge. In yet other embodiments, the apparatus includes a substrate; a plurality of hollow tubes (e.g., needles) affixed to the substrate and configured to be at least partially inserted into a biological tissue; at least one opening provided on or in a wall of each of the hollow tubes; at least one cutting edge protruding from the wall of each of the hollow tubes proximal to the at least one opening; and a sleeve provided around at least a portion of each of the tubes, where each tube is configured to be translatable along a longitudinal axis of a corresponding sleeve, and where a distance from the longitudinal axis of each tube to an outer edge of each corresponding sleeve is at least as large as a distance from the longitudinal axis of the tube to an outer portion of the cutting edge of the tube.

The procedures herein can include one or more optional processes that promote effective incision or excision of tissue portions or that benefit healing. Such optional processes include cooling, freezing, or partially freezing the skin portion prior to skin incision or excision (e.g., by applying a cryospray or by contacting a surface of a skin region with a cooled object for an appropriate duration), where such cooling and/or freezing can, e.g., increase mechanical stability of the tissue portions; treatment with red or near-infrared light of the skin portion to further promote healing of the tissue; and/or treatment with an optical energy source, such as any described herein (e.g., an ablative laser).

Exemplary procedures, methods, and apparatuses are provided in U.S. Pub. Nos. 2012/0041430, 2011/0313429, 2011/0251602, 2012/0226214, 2012/0226306 and 2012/0226214; International Pub. Nos. WO 2012/103492, WO 2012/103483, WO 2012/103488, WO 2013/013199, WO 2013/013196, and WO 2012/119131; Fernandes et al., "Micro-Mechanical Fractional Skin Rejuvenation," Plastic &Reconstructive Surgery 130(55-1):28 (2012); and Fernandes et al., "Micro-Mechanical Fractional Skin Rejuvenation," Plastic & Reconstructive Surgery 131(2):216-223 (2013), where each is hereby incorporated by reference in its entirety.

Examples

Example 1: Method of Treating Skin Regions

A skin region can be treated by any useful method prior to affixing a dressing. For example, this method can include forming a plurality of small holes is in the skin through the dermal and epidermal layer. Generally, the dimension of the holes is in the range of 50-500 pm in diameter. Without wishing to be limited by theory, it is envisioned that up to 40% of the treated skin surface can be removed and that the amount of removed skin determines the extent of the tightening effect. The holes can be formed surgically, for example, by using a hollow coring needle (e.g., any described herein). Alternative forms of energy, e.g., such as laser, non-coherent light, radio-frequency, or ultrasound, can also be used to form the holes. The holes can be circular or have any other preferred shape (e.g., an elongated shape). After the formation of such holes, the methods and devices (e.g., dressings) described herein (e.g., in the following Examples) can be employed to reduce skin surface and/or tighten skin.

Example 2: Exemplary Tunable Dressing Affixed to the Skin in a Tensionless State and then Activated to Compress the Skin (Method 1)

After treating the skin to form a plurality of holes in a skin portion, a tunable dressing can be used to compress the skin.

In one embodiment, the dressing comprises an adhesive layer that is in contact with the skin and a tension-regulation layer (a regulatable layer) that is affixed to the adhesive layer. The tension-regulation layer allows adjustment of the dimension of the dressing in the plane of the dressing (e.g., parallel to the skin in the x-direction in FIG. 1 or in the y-direction (not shown in FIGS. 1A-1D)). Other functional layers include those providing occlusion to control humidity and/or to promote moisture-enhanced wound healing, absorption of wound exudate, delivery of drugs, etc., which can be added to the dressing.

In particular embodiments, the dressing is applied on a treated skin area in a tensionless state. At that stage, the dressing does not apply any lateral force on the small wounds or holes. The regulatable layer is then activated, altering the geometry of the dressing. The dressing shrinks and applies a lateral force closing the small wounds.

FIG. 1 describes this exemplary process. Holes, e.g., microscopic holes 101, are formed through the dermal and epidermal layer 102 above fatty layer 103 (step A, FIG. 1A). The dressing comprising adhesive 104 and tension-regulation layer 105 is applied on the holes in a tensionless state and adheres to the skin surface (step B, FIG. 1B). The tension-regulation layer 105 of the dressing is activated, altering the dimension of the dressing (shrinking). The shrinking dressing applies a lateral compression force 120 on the small holes, and the lateral compression force closes the holes 101 (step C, FIG. 1C). Any remaining space in the holes fills with new tissue 106 and completes the healing process (step D, FIG. 1D).

The tension-regulation layer can any useful material, e.g., a stimulus-responsive polymer, such as a shape-memory material or any described herein. Stimulus-responsive polymers are materials that can change properties with variation of their environment. For example, geometrical and mechanical properties of certain types of polymers can change in response to changes in temperature, pH, light, moisture, magnetic field. Shape-memory polymers are stimulus-responsive polymers and exhibit similar behaviors as shape-memory alloys; their dimension and elastic properties respond to changes in temperature. Fabrics constituted of shape-memory polymers can be manufactured by knitting and weaving of shape-memory polymer fibers. Exemplary fabrics and polymers are described herein, as well as in Hu et al., "A review of stimuli-responsive polymers for smart textile applications," Smart Mater. Struct. 21: article 053001 (2012), which is hereby incorporate by reference. In particular embodiments, the regulatable layer includes a woven article having a shape-memory polymer (SMP), which has a first shape (i.e., before exposure to temperature above the activation threshold) and a second shape (i.e., after exposure to temperature above the activation threshold), and contraction occurs upon exposure to a temperature greater than glass transition temperature of the SMP. Increasing the temperature of the material above a pre-determined threshold above body temperature, for example by using a blowgun, can shorten the fibers irreversibly (i.e., by decreasing the temperature below the threshold does not have any impact on the fibers length), therefore contracting the dressing. The SMP composition can be optimized to have a particular temperature threshold and response to the change in temperature.

Shape-memory materials, e.g., SM Ps, can be programmed with another low temperature threshold below room temperature that reverts dimensional changes observed after exposure to temperature above the high temperature threshold. This mechanism allows the user to expand the dressing, for example, if the dressing is too tight after high-temperature contraction. The dressing temperature can be altered for example by using a cooling blowgun or by applying a cold surface on the dressing.

Example 3: Exemplary Tunable Dressing Including a Shape-Memory Alloy (Method 1)

The dressing can include any useful material in the regulatable layer. In one embodiment, the tension-regulation layer can integrate a shape-memory alloy (SMA) material in any useful form, e.g., in the form of wires. The SMA can be geometrically arranged, and its mechanical properties can be optimized to respond to particular changes in temperature. In one non-limiting embodiment, a network of SMA wires is arranged in the regulatable layer, e.g., tension-regulation layer 105, e.g., a grid of SMA wires 201, as shown in FIG. 2.

Similar to the dressing in the above-described example, elevation of temperature can irreversibly alter the wound-dressing geometry, and the SMA can be programmed with another low temperature threshold below room temperature that reverts dimensional changes observed after exposure to temperature above the high temperature threshold. In this manner, a user can expand the dressing, for example, if the dressing is too tight after high-temperature contraction.

The entire dressing or a portion of the dressing (e.g., a limited surface of the dressing) can be activated or tuned, such as by heating the dressing locally when a thermal-responsive material (e.g., a shape-memory alloy) is used. The level of activation of the dressing can also be varied by the level of heating, e.g., heating the entire thermally-responsive material or the entire grid including such a material will result in full activation, while partial heating will result in partial activation. In other words, the level of skin tightening can be controlled gradually (e.g., in intensity) and spatially (e.g., in the x-, y-, z-, xy-, xz-, yz-, or xyz-direction).

Having described dressing including an SMP and/or SMA in the above examples, the same concept can be applied with one or more other stimuli, for example, moisture, solvent, pH, light, electric field, and/or magnetic field, by using any useful material (e.g., as described herein).

Having described exemplary dressing including fibers or grids of an SMP and/or SMA, other form factors can be envisioned for the stimulus-responsive material. Exemplary forms of such materials include a film, a membrane (e.g., as in temperature shrink wrap), or an actuator having more complex geometries.

Example 4: Methods of Tightening of the Skin in a Preferred Direction (Method 2)

The present invention also includes methods of tightening skin in a preferred direction. It might be advantageous to tighten the skin in a pre-determined direction, for example, in the case of a breast lift or an eyebrow lift. In one particular example, it is advantageous to close ablations following Langer lines. FIG. 3 shows the skin surface (top view, x-y plane) (in FIG. 3A) before closure of the small holes, (in FIG. 3B) after non-directional tightening, and (in FIG. 3C) after directional tightening along the x-axis. In FIG. 3B, the holes 101 are closed by pulling tissue from all directions, thereby resulting in partial hole closure with in holes of smaller diameter. The tightening effect is not directional. In FIG. 3C, the holes 101 are closed by pulling tissue along the x-axis, thereby resulting in partial hole closure with elliptical holes having their long axis along the y-axis. Thus, the tightening effect is unidirectional along the x axis.

The mechanism proposed in Method 1 (Examples 2 and 3) would result in non-directional tightening. The dressing concept can easily be modified to provide unidirectional tightening, for example, by aligning the shape-memory polymer fibers along the preferred direction of tightening. Activation of the fibers (i.e., fibers shortening) results in a compression of the dressing along the axis of the fibers. The same concept can be applied to shape-memory alloy wires or other actuators having a preferred direction of contraction. FIG. 4A shows an exemplary dressing that integrates a grid of shape-memory alloy wires 201. Contraction of the wires results in non-directional tightening. FIG. 4B shows the wires aligned in a single-direction arrangement 401. Contraction of the wires results in directional tightening, aligned with the wires. The contraction of the dressing along the x- and y-axis of the dressing shown in FIG. 5 below can be controlled independently. For example, a grid of two different stimulus-responsive polymers 501 can be integrated in the tension-regulation layer 105 (FIG. 5). Polymer fibers 502 compressing the dressing along the x-axis responds to a first stimulus (stimulus A), while another type of polymer fibers 503 compress the dressing along the y-axis and respond to a different stimulus (stimulus B). For example, stimulus A can be thermal (e.g., by using a thermal-responsive material, such as any described herein), while stimulus B is pH (e.g., by using a pH-responsive material, such as any described herein).

An alternative embodiment includes a dressing that expands in a direction perpendicular to the direction of tightening. In FIG. 3, the dressing expands the skin along the y-axis, resulting in closure of the holes along the x-axis. The dressing concept proposed in Method 1 (Examples 2 and 3) can be modified by integrating a material that expands along an axis in the tension regulation layer (instead of contracting). Stimulus-responsive polymers can be programmed to expand when exposed to pre-determined stimulus. Actuators expanding along an axis can also be integrated in the regulatable layer of the dressing.

Example 5: Exemplary Tunable Dressing that Compresses the Skin in a Preferred Compression State (Method 3)

When using dressing to compress the skin and close the holes, it might be advantageous to apply an optimal compression level. Tissue can be compressed by a wound dressing as described above in Method 1. The state of the tissue provides feedback about the optimal compression level. For example, it might be advantageous to close the holes but control or regulate the extent of tissue pleating. Tissue pleating might affect the wound healing process. FIG. 6 shows the effect of pleating on hole geometry. Constraints applied on the walls of the holes at the top of pleats, e.g., hole 601, tend to keep the hole open, therefore increasing healing time and the risk of scar formation. Constraints applied on the walls of the hole at the bottom of the pleats, e.g., hole 602, tend to close the hole. Constraints applied on the walls of the hole on a side of the pleats, e.g., hole 603, have no effect on the hole. In addition, pleating may prevent conformal adhesion of the wound dressing with the treated skin, therefore affecting the proper function of the wound dressing that needs to be in contact with the skin. These methods and devices are applicable not only to compress and expand holes in the skin region but also to compress and expand slits in the skin region. Pleating can be controlled by inspection of the skin during dressing activation. Activation can be stopped when the tissue reaches a compression level that starts causing pleating. Alternatively, the dressing can control pleating by having limited flexibility. Accordingly, the methods and devices described herein can be useful for controlling pleating (i.e., increasing and/or decreasing the extent of pleating).

Example 6: Methods Including Elongated Holes to Promote Healing and Directional Tightening (Method 4)

The present invention also includes optimizing the dimension of the incised or excised tissue portions to promote wound healing. It might be advantageous to generate small holes that are not circular to promote wound healing. For example, pre-stretching the skin before treatment with a circular coring needle generates an elliptical hole in a non-stretched skin. The long axis of the ellipse is perpendicular to the pre-stretching direction. An elliptical hole can generate skin tightening preferentially in the direction of the short axis of the ellipse. Accordingly, the devices of the invention (e.g., a. dressing, as described herein) can be affixed to a skin portion including one or more elliptical holes or one or more incised or excised tissue portions having one or more elliptical geometries.

Other Embodiments

All publications, patent applications, and patents mentioned in this specification are herein incorporated by reference.

Various modifications and variations of the described method and system of the invention will be apparent to those skilled in the art without departing from the scope and spirit of the invention. Although the invention has been described in connection with specific desired embodiments, it should be understood that the invention as claimed should not be unduly limited to such specific embodiments. Indeed, various modifications of the described modes for carrying out the invention that are obvious to those skilled in the fields of medicine, pharmacology, or related fields are intended to be within the scope of the invention.

What is claimed is:

1. A method of skin tightening comprising:
    (i) producing a plurality of excised tissue portions in a region of skin tissue using a system comprising,
        a plurality of tubes configured to contact a surface of the skin to generate holes in the skin tissue by excising portions of the skin tissue;
        a first actuator configured to rotate and/or translate the plurality of tubes relative to the skin; and
        a suction or pressure system to facilitate removal of tissue portions from the plurality of tubes; and
    (ii) affixing to the skin region a device that provides contraction or expansion of said skin region in one or more directions;
    wherein at least one of said excised tissue portions has at least one dimension that is less than 2 mm.

2. The method of claim 1, wherein at least one of said excised tissue portions has a length of more than 1 mm.

3. The method of claim 1, wherein at least one of said excised tissue portions has a length of about 3.5 mm.

4. The method of claim 1, wherein an areal fraction of excised tissue portions is less than about 70% of the skin region.

5. The method of claim 1, wherein an areal fraction of excised tissue portions is less than about 10% of the skin region.

6. The method of claim 1, wherein said plurality of excised tissue portions comprise one or more elliptical holes in said skin region.

7. The method of claim 1, wherein said affixing step (ii) is performed within about 30 seconds of excising said skin region.

8. The method of claim 1, wherein said affixing step (ii) is performed within about ten seconds of excising said skin region.

9. The method of claim 1, wherein said method results in controlling pleating in said skin region.

10. The method of claim 1, wherein the device is or comprises a dressing.

11. The method of claim 1, wherein the device comprises an adhesive material.

12. The method of claim 1, wherein the device comprises an unstretched material.

13. The method of claim 1, wherein the affixing the device to a skin region provides contraction of said skin region in one direction.

14. The method of claim 1, wherein the device comprises one or more shape memory polymer fibers or wires, and wherein contraction of said skin region is provided by aligning the one or more shape memory polymer fibers or wires along one direction.

15. The method of claim 1, further comprising increasing a temperature of the device above a pre-determined threshold above body temperature.

16. The method of claim 1, further comprising exposing the device to one or more stimuli selected from a group consisting of moisture, solvent, pH, light, electric field, and magnetic field.

17. The method of claim 1, further comprising adjusting contraction or expansion of said skin region to minimize or prevent skin pleating.

18. The method of claim 1, further comprising pre-stretching the skin region before producing the plurality of excised tissue portions.

19. The method of claim 1, comprising pre-stretching the skin region before producing the plurality of excised tissue portions with a circular coring needle to generate an elliptical hole in the skin region when the skin region is not stretched.

20. The method of claim 1, wherein the skin region is located on a face, eyelid, cheek, chin, forehead, lips, nose, neck, chest, arm, leg, and/or a back.

21. A system for skin tightening comprising:
a plurality of tubes configured to contact a surface of the skin to generate holes in skin tissue by excising portions of the skin tissue;
a first actuator configured to rotate the plurality of tubes relative to the skin;
a suction or pressure system to facilitate removal of skin portions from the tubes;
a stop arrangement to control the depth of the excision and/or the length of the excised tissue portions, wherein the stop arrangement is adjustable along a long axis of at least one of the plurality of tubes to control the depth of excision in the skin; and
a device affixable to a skin region comprising a plurality of the excised tissue portions, wherein said device provides contraction or expansion of said skin region in one or more directions.

22. The system of claim 21, wherein the first actuator is further configured to translate the plurality of tubes relative to the skin.

23. The system of claim 21, further comprising a second actuator configured to translate the plurality of tubes relative to the skin.

24. The system of claim 21, wherein the plurality of tubes comprises between 10 and 20 tubes.

25. The system of claim 21, wherein the plurality of tubes comprises nine tubes.

26. A method of skin tightening comprising:
(i) producing a plurality of excised tissue portions in a region of skin tissue using a system comprising,
a plurality of hollow tubes configured to contact a surface of the skin to generate holes in the skin tissue by excising portions of the skin tissue, which hollow tubes have an inner diameter that is less than 0.5 mm;
a first actuator configured to rotate and/or translate the plurality of tubes relative to the skin; and
a suction or pressure system to facilitate removal of tissue portions from the plurality of hollow tubes; and
(ii) affixing to the skin region a device that provides contraction or expansion of said skin region in one or more directions.

27. A method of skin tightening comprising:
(i) rotating and/or translating a plurality of tubes relative to a skin tissue, and contacting the tubes with a surface of the skin tissue, thereby excising from a region of the skin tissue one or more tissue portions having at least one dimension that is less than 2 mm into the tubes; and
applying a suction or pressure force to facilitate removal of the excised tissue portions from the tubes; and
(ii) affixing a device to the region, wherein said device provides contraction or expansion of said region in one or more directions.

* * * * *